United States Patent [19]

Immer et al.

[11] 4,010,260
[45] Mar. 1, 1977

[54] DERIVATIVES OF RETRO-ENANTIO-SOMATOSTATIN, INTERMEDIATES THEREFOR, AND PROCESS THEREFOR

[75] Inventors: Hans U. Immer, Mount Royal; Nedumparambil A. Abraham, Dollard des Ormeaux; Verner R. Nelson, Kirkland, all of Canada

[73] Assignee: Ayerst McKenna & Harrison Ltd., Montreal, Canada

[22] Filed: July 28, 1975

[21] Appl. No.: 599,448

[52] U.S. Cl. .......................... 424/177; 260/112.5 S
[51] Int. Cl.² ............... C07C 103/52; A61K 37/00
[58] Field of Search ............................. 260/112.5 S

[56] References Cited

UNITED STATES PATENTS 3,933,784   1/1976   Sarantakis ................. 260/112.5 S

*Primary Examiner*—Lewis Gotts
*Assistant Examiner*—Reginald J. Suyat
*Attorney, Agent, or Firm*—Stephen Venetianer

[57] ABSTRACT

Compounds of the formula 1 or 1a

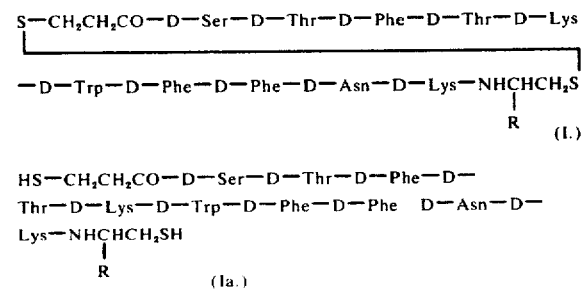
(I.)

HS—CH₂CH₂CO—D—Ser—D—Thr—D—Phe—D—
Thr—D—Lys—D—Trp—D—Phe—D—Phe   D—Asn—D—
Lys—NHCHCH₂SH
         |
         R           (1a.)

in which R is hydrogen or CONHCH₂CONHCH₂CH₃ are disclosed. The compounds are obtained by a process which comprises the following step: preparing peptide fragments II, III, V and VII see below, by a series of condensations involving the reaction of an appropriately protected peptide having an activated ester group with an appropriately protected peptide having a free amino group; condensing

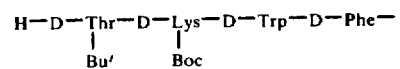
(II)

by means of the azide method with

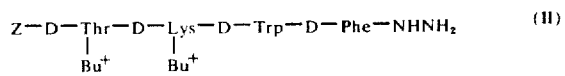
(III)

followed by hydrogenolysis of the reaction product to obtain

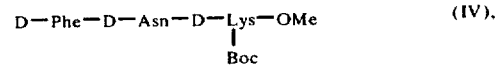

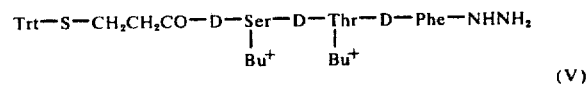
(IV), condensing the latter by means of the azide method with

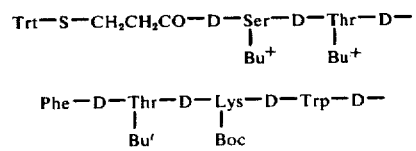
(V)

followed by treating the resulting compound with hydrazine hydrate to obtain

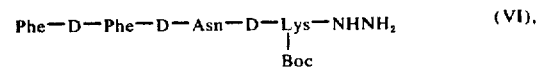

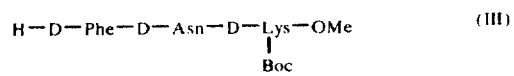

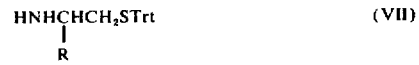
(VI), condensing the latter by means of the azide method with HNHCHCH₂STrt
    |
    R           (VII)

in which R is hydrogen or CONHCH₂CONHCH₂CH₃ to obtain the linear protected peptide

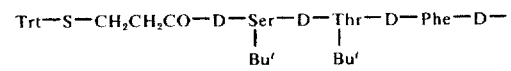

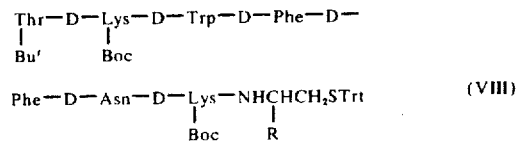
(VIII)

in which R is as defined herein; thereafter said linear peptide is transformed into the desired cyclic peptide of formula 1 by deprotecting and oxidizing processes. In addition, the linear, reduced form of the peptide of formula 1a is obtained by deprotection of the aforementioned linear peptide or by reduction of the cyclic peptide. The peptides of formulae 1 and 1a are useful for the management of diabetes and the treatment of acromegaly. Methods for their use are also disclosed.

52 Claims, No Drawings

DERIVATIVES OF RETRO-ENANTIO-SOMATOSTATIN, INTERMEDIATES THEREFOR, AND PROCESS THEREFOR

BACKGROUND OF THIS INVENTION a. Field of Invention

This invention relates to derivatives of the tetradecapeptide somatostatin. More particularly, this invention concerns peptide derivatives of retro-enantio-somatostatin and salts thereof, a process for preparing the peptide derivatives and salts, intermediates used in the process and methods for using the peptide derivatives and their salts.

b. Prior Art

The name "somatostatin" has been proposed for the factor found in hypothalamic extracts which inhibits the secretion of growth hormone (somatotropin). The structure of this factor has been elucidated by P. Brazeau, et al., Science, 179, 77 (1973) and reported to be the following tetradecapeptide structure:

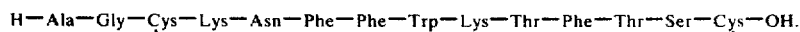

The abbreviations used herein for the various amino acids are Ala, alanine; Asn, asparagine; Cys, cysteine; Gly, glycine; Lys, lysine; Phe, phenylalanine; Ser, serine; Thr, threonine; and Trp, tryptophane.

The constitution of the tetradecapeptide somatostatin has been confirmed by synthesis; for example, see D. Sarantakis and W. A. McKinley, Biochem. Biophys. Res. Comm., 54, 234 (1973), J. Rivier, et al., Compt. Rend. Ser. D, 276, 2737 (1973) and H.U. Immer et al., Helv. Chim. Acta, 57, 730 (1974).

The important physiological activity of this tetradecapeptide established it as a compound of significance for clinical pharmacology relating to the treatment of acromegaly and the management of diabetes; for example, see K. Lundbaek, et al., Lancet, 2, 131 (1970) and R. Guillemin in "Chemistry and Biology of Peptides" J. Meienhofer, Ed., 3rd American Peptide Symposium Boston 1972, Ann Arbor Science Publications, Ann Arbor, Mich., 1972, pp 585 –600.

The linear form of somatostatin, having two sulfhydryl groups instead of a disulfide bridge, has been prepared recently by J.W.F. Rivier, J. Amer. Chem. Soc., 96, 2986 (1974). He reports that the linear form is equipotent to somatostatin based on the ability of the two compounds to inhibit the rate of secretion of growth hormone by rat pituitary cells in monolayer tissue cultures.

Only recently have there been reported polypeptides, other than the natural hormone and its linear form, having somatostatin-like activity. D. Sarantakis, et al., Biochem. Biophys. Res. Comm., 55, 538 (1973) reported the synthesis of the somatostatin analog, [Ala$^{3,14}$]-somatostatin, by solid phase methods. This analog exhibited a very small amount of activity, about 0.01% of somatostatin's potency. P. Brazeau, et al., Biochem. Biophys. Res. Comm., 60, 1202 (1974) recently reported the synthesis of a number of acylated des[Ala$^1$-Gly$^2$]-somatostatin compounds, by solid phase methods.

The present invention discloses new analogs of somatostatin based on the principle of the retro-enantio system. This system is achieved by construction of a reversed sequence of amino acids having opposite configuration, i.e., D instead of L, to give the "retro-enantio" isomer of the natural peptide. It is surprising that the retro-enantio derivatives of somatostatin of formulae I or Ia have been found to retain the activity of the natural hormone somatostatin notwithstanding the fact that other hormones of the retro-enantio system have shown a range of retention of full activity to complete loss of activity, as reported in the review by J. Rudinger, The Design of Peptide Hormone Analogs, pp 368 –369 in Drug Design, Vol. II, Ed. E.J. Ariens, Academic Press, New York and London, 1971.

The present invention discloses retro-enantio peptide derivatives which retain the activity of the natural hormone somatostatin. The derivatives are prepared readily by a convenient process, which includes the following advantages: the process starts from readily available materials, avoids noxious reagents, is executed facilely and utilizes easily removable protecting groups.

The foregoing advantages and attributes render the peptides of this invention useful for the management of diabetes and the treatment of acromegaly.

SUMMARY OF THE INVENTION

The peptides of this invention are represented by formulae I and Ia; formula I representing the cyclic peptides of this invention and formula Ia representing the linear reduced form

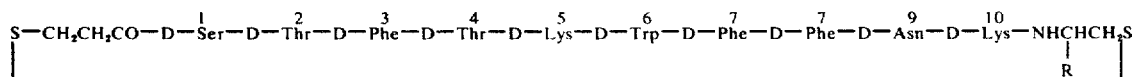

(I)

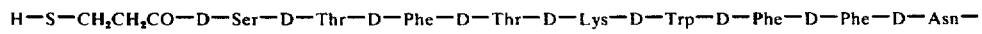

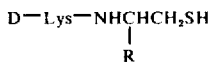

(Ia)

in which R is hydrogen or CONHCH$_2$CONHCH$_2$CH$_3$.

When R is CONHCH$_2$CONHCH$_2$CH$_3$, the terminal group

CONHCH$_2$CONHCH$_2$CH$_3$, the terminal group NHCHCH$_2$S
| 
R may be written alternatively as D-Cys-Gly-NHEt, and formulae I and Ia may be written as

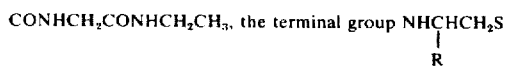

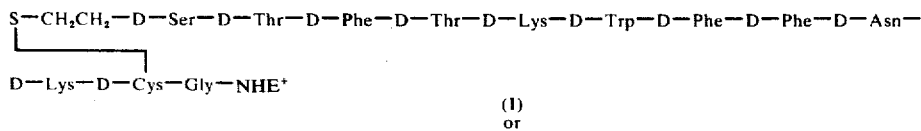

(I)

or

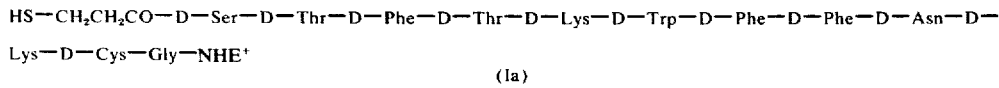

(Ia)

The pharmaceutically acceptable salts of the compounds of formulae I and Ia are also included within the scope of this invention.

The peptides of this invention are prepared by a process comprising:

Preparing peptide fragments II, III, IV, V, VI and VII, see below, by a series of condensations involving the reaction of an appropriately protected peptide having an activated ester group with an appropriately protected peptide having a free amino group.

The tetrapeptide of formula

containing the amino and residues 4–7 is condensed by means of the azide method with a tripeptide (8–10) of formula H—D—Phe—D—Asn—D—Lys—OMe (III)
|
Boc to yield the heptapeptide (4–10) of formula Z—D—Thr—D—Lys—D—Trp—D—Phe—D—Phe—D—Asn—D—Lys—OMe.
|      |                                            |
Bu$^+$  Boc                                          Boc The latter is hydrogenolized by means of hydrogen and a noble metal catalyst to yield the heptapeptide (4–10) of formula

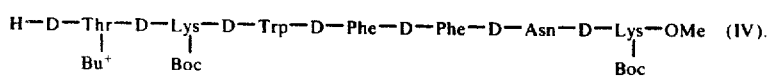

Said last-named compound (IV) is condensed by means of the azide method with the tripeptide (1–3) of formula Trt—S—CH$_2$CH$_2$CO—D—Ser—D—Thr—D—Phe—NHNH$_2$
                        |      |
                        Bu$^+$  Bu$^+$                            (V)

to yield the decapeptide of formula

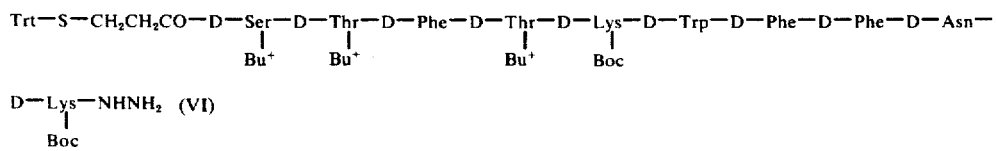

D—Lys—NHNH$_2$ (VI)
|
Boc containing the amino acid residues 1 – 10.

Said last-named compound (VI) is condensed by means of the azide method with

HNHCHCH$_2$STrt                                     (VII)
|
R in which R is hydrogen (VIIa) or CONHCH$_2$CONHCH$_2$CH$_3$ (VIIb) to yield the linear protected peptide of formula (VIII)

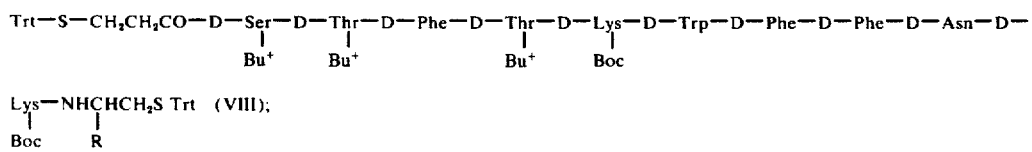

Lys—NHCHCH$_2$S Trt  (VIII);
|          |
Boc        R in which R is as defined herein followed by oxidizing said linear protected peptide (VIII) with iodine or thiocyanogen to obtain the corresponding cyclic disulfide of formula (IX)

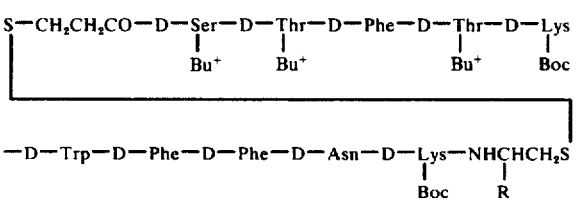

in which R is as defined herein and subsequently removing all remaining protecting groups under moderately acidic conditions to obtain the corresponding peptide of formula I; or followed by subjecting said linear peptide of formula (VIII) to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative by treatment with hydrogen sulfide, oxidizing said last-named derivative by treatment with oxygen, 1,2-diiodoethane, sodium or potassium ferricyanide or iodine to obtain the corresponding cyclic disulfide derivative, and removing the remaining protecting groups under moderately acidic conditions to obtain the desired peptide of formula I. Alternatively, said cyclic disulfide derivative is reduced to said corresponding free disulfhydryl derivative by agents known to be effective for reducing known cyclic disulfides to their corresponding disulfhydryl derivatives.

A further aspect of this invention comprises the removal of all the protecting groups from the aforementioned linear protected peptide of formula (VIII) or the aforementioned disulfhydryl derivatives under moderately acidic conditions to obtain the linear reduced form of the peptide of this invention of formula Ia, benzyloxycarbonyl (represented by Z), t-butyloxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, or ethoxycarbonyl; the acyl type protecting groups which include formyl, trifluoroacetyl, phthalyl, acetyl, or toluenesulfonyl; the alkyl type protecting groups which include triphenylmethyl or trityl (represented by Trt) or benzyl. The preferred protecting groups are benzyloxycarbonyl, t-butyloxycarbonyl, triphenylmethyl and α,α-dimethyl-3,5-dimethoxybenzyloxycarbonyl. The protecting groups for the hydroxyl of serine and tyrosine are represented by acetyl, tosyl, benzoyl, tert-butyl (represented by $Bu^+$), trityl, and benzyl. The preferred protecting group is tert-butyl. The protecting group on the sulfur of cysteine or modified cysteine is illustrated by benzyl, triphenylmethyl or trityl (represented by Trt), benzyloxycarbonyl, or acetamidomethyl (represented by Acm), the preferred protecting groups are trityl and acetamidomethyl. The carboxylic acid function of a peptide or amino acid can be considered protected by lower alkyl or lower aralkyl esters which include methyl (represented by OME), ethyl (repre-

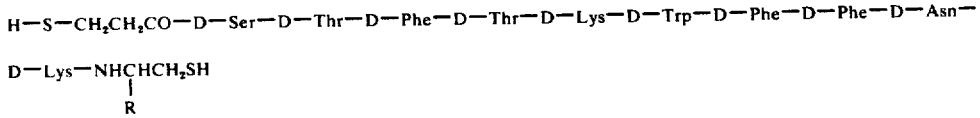

in which R is as defined herein.

The latter compound is also obtained by direct reduction of the cyclic peptide of formula I by agents known to be effective for reducing known cyclic disulfides to their corresponding disulfhydryl derivatives. If desired said reduced form of the cyclic peptide is converted to the corresponding derivative of formula I by one of the above oxidizing agents.

DETAILS OF THE INVENTION

In general, the abbreviations used herein for designating the amino acids and the protective groups are based on recommendations of the IUPAC-IUB Commission on Biochemical Nomenclature, see Biochemistry, II, 1726–1732 (1972). For instance, Gly, Cys, Lys, Asn, Phe, Trp, Thr, and Ser represent the "residues" of glycine, cysteine, lysine, asparagine, phenylalanine, tryptophane, threonine and serine, respectively. By the residue is meant a radial derived from the corresponding D-amino acid by eliminating the OH portion of the carboxyl group and the H portion of the amino group. All the amino acids have the unnatural D-configuration.

A number of procedures or techniques for the preparation of peptides have hitherto been well established. For instance, the functional groups which are not involved in the peptide bond formation reaction are optionally protected by a protecting group or groups prior to the condensation reaction. For example, protecting groups which may be chosen for an amino function of a peptide or amino acid not involved in the peptide bond formation are: the alkoxycarbonyls which include sented by OEt), or benzyl (represented by OBzl), and also by substituted hydrazides which include t-butyloxycarbonyl hydrazide (represented by NHNH Boc), benzyloxycarbonyl hydrazide (represented by NHNH Z), or α,α-dimethyl-3,5-dimethoxybenzyloxycarbonyl hydrazide (represented by NHNH Ddz).

To promote facile condensation of the peptide carboxyl group with a free amino group of another peptide to form a new peptide bond, the terminal carboxyl group must be activated. Descriptions of such carboxyl-activating groups are found in general textbooks of peptide chemistry; for example K.D. Kopple, "Peptides and Amino Acids", W.A. Benjamin, Inc., New York, 1966, pp. 45 –51 and E. Schroder and K. Lubke, "The Peptides"; Vol. I, Academic Press, New York, 1965, pp. 77 –128. Examples of the activated form of the terminal carboxyl are acid chloride, anhydride, azide, activated ester, or o-acyl urea of a dialkylcarbodiimide. The following activated esters have proved to be particularly suitable in the process of this invention: 2,4,5-trichlorophenyl (represented by OTcp), pentachlorophenyl (represented by OPcp), p-nitrophenyl (represented by ONp), or I-benzotriazolyl. The succinimido group is also useful for activating a carboxyl.

The term "azide method" as used herein refers to the method of coupling two peptide fragments which comprises the reaction of a peptide hydrazide with a reagent which furnishes nitrous acid in situ. Suitable reagents for this purpose include organic nitrites (e.g. t-butyl nitrite, isoamyl nitrite) or an alkali metal nitrite salt (e.g. sodium nitrite, potassium nitrite) in the presence of a strong acid such as hydrogen chloride or sulfuric or phosphoric acid. The corresponding peptide azide thus obtained is then reacted with a peptide having a free amino group to obtain the desired peptide. Preferred conditions for the azide method of coupling comprises reacting the peptide hydrazide with nitrous acid, generated in situ from an organic nitrite in the presence of a mineral acid, preferably hydrogen chloride (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like at −30° to 20° C, preferably at about −15° C, for 10 to 30 minutes to obtain the corresponding azide. The peptide azide can be isolated and crystallized or is preferably allowed to remain in the reaction mixture, and thereafter reacting the azide in the said mixture with the peptide unit having the free amino group at temperatures ranging from −30° to 20° C for about one to two hours and then at 0° to 30° C for 10 to 30 hours. An acid acceptor, preferably an organic base, for example N-ethyldiisopropylamine, N-ethylmorpholine or triethylamine, is present in the reaction medium in order to make the reaction medium slightly alkaline, preferably pH 7.0 to 7.5. See also the above cited textbooks of Kopple or Schroder and Lubke for additional descriptions of this method.

The terms "peptide, polypeptide, tripeptide, hexapeptide, and the like" as used herein are not limited to refer to the respective parent peptides but also are used in reference to modified peptides having functionalized or protecting groups. The term "peptide" as used herein is used in reference to a peptide with two to twelve amino acid residues. In addition the residue

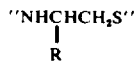

as defined herein is written as H-D-Cys-Gly-NHEt when R is $CONHCH_2CONHCH_2CH_3$, and is written as a modified residue of cysteine when R is H, viz., 2-thioethylamine.

The abbreviation Me represents a methyl group and $NHNH_2$ represents a hydrazide group. In addition, the following abbreviations are used: dimethylformamide (DMF), tetrahydrofuran (THF), dimethyl sulfoxide (DMSO), methanol (MeOH), ethyl acetate (EtOAc), methylene dichloride ($CH_2Cl_2$), N,N'-dicyclohexylcarbodiimide (DCC), sodium chloride (NaCl), sodium bicarbonate ($NaHCO_3$), sodium sulfate ($Na_2SO_4$) magnesium sulfate ($MgSO_4$), and 5% palladium on charcoal (5% Pd/C).

The term lower akyl as used herein contemplates hydrocarbon radicals having one to three carbon atoms and includes methyl, ethyl and propyl.

The term mineral acid as used herein contemplates the strong inorganic acids and includes hydrochloric, hydrobromic, sulfuric, phosphoric and the like. When the term is used in conjunction with an anhydrous system, hydrogen chloride is the preferred mineral acid.

The term mildly acidic conditions as used herein contemplates conditions in which a dilute aqueous solution of an organic acic, for example 30 − 80% or mixtures thereof, is a principal component of the reaction medium.

The term moderately acidic conditions as used herein contemplates conditions in which concentrated organic acids or aqueous solutions of the mineral acids are used as a principal component of the reaction medium at temperatures ranging from about −30° to 30° C. Examples of preferred conditions in this case include the use of 50 to 100% trifluoroacetic acid at 0° to 30° C or 0.1 − 12N hydrochloric acid in aqueous or anhydrous organic solvents at −20° to 10° C.

The term organic nitrite includes the commercially available alkyl nitrites, for instance, t-butyl nitrite or isoamyl nitrite.

The term organic base as used herein includes triethylamine, N-ethylmorpholine, or N-ethyldiisopropylamine.

The term strong base as used herein contemplates both organic bases, as described above, and strong inorganic bases including the hydroxides and carbonates of sodium and potassium.

The peptides of this invention, including the cyclic and the linear reduced forms, are obtained in the form of the free base or as an acid addition salt thereof either directly from the process of this invention or by reacting the peptide with one or more equivalents of the appropriate acid. Examples of preferred salts are those with pharmaceutically acceptable organic acids, e.g. acetic, lactic, succinic, benzoic, salicylic, methanesulfonic or toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. It should be noted that the peptides have two basic nitrogens giving rise to addition salts with one to possibly two equivalents of acid. If desired a particular acid addition salt is converted into another acid addition salt, e.g., a salt with a non-toxic, pharmaceutically acceptable acid, by treatment with the appropriate ion exchange resin in the manner described by R. A. Boissonas, et al., Helv. Chim. Acta, 43, 1349 (1960). Suitable ion exchange resins are cellulose based cation exchangers, for example carboxymethylcellulose or chemically modified, cross-linked dextran cation exchangers, for example, those of the Sephadex C type, and strongly basic anion exchange resins, for example those listed in J. P. Greenstein and M. Winitz "Chemistry of the Amino Acids", John Wiley and Sons, Inc., New York and London, 1961, Vol. 2, p. 1456.

The peptides of this invention of formulae 1 and 1a give complex salts with heavy metal ions. An example of a pharmaceutically acceptable heavy metal complex is a complex formed with zinc or with zinc protamine.

The peptides of formulae 1 or 1a, as well as their corresponding pharmaceutically acceptable salts, are useful because they possess the pharmacological activity of the natural hormone somatostatin. Their activity is demonstrated readily in pharmacological tests such as a modification [A. V. Schally, et al., Biochem. Biophys. Res. Commun., 52, 1314 (1973); J. Rivier, et al., C.R. Acad. Sci. Paris, Ser. D., 276, 2737 (1973)] of the in vitro method of M. Saffran and A. V. Schally, Can. J. Biochem. Physiol., 33, 405 (1955).

The activity of the peptides of formulae 1 or 1a is demonstrated also in vivo in a modification of the pentobarbital-induced increase in plasma growth hormone level in the rat as described by Brazeau, et al., cited above. In this test the peptides of this invention show a level of activity which is of the same order as that of somatostatin.

The peptides of formulae 1 or 1a and their salts are useful for the treatment of acromegaly and other hypersecretory endocrine states and in the management of diabetes in mammals; see for example, P. Brazeau, et al., cited above. When a peptide of formula 1 or 1a or a salt thereof is employed for such treatment or management, it is administered systemically, preferably parenterally, in combination with a pharmaceutically acceptable liquid or solid carrier. The proportion of the peptide or salt thereof is determined by its solubility in the given carrier, by the given carrier, or by the chosen route of administration, and by standard biological practice. For parenteral administration to animals the peptide or a salt thereof is used in a sterile aqueous solution which may also contain other solutes such as buffers or preservatives, as well as sufficient pharmaceutically acceptable salts or glucose to make the solution isotonic. The dosage will vary with the form of administration and with the particular species of animal to be treated and is preferably kept at a level of from 5 mcg to 300 mcg per kilogram body weight. However, a dosage level in the range of from about 10 mcg to about 50 mcg per kilogram body weight is most desirably employed in order to achieve effective results.

The peptides or salts thereof may also be administered in one of the long acting, slow-release or depot dosage forms described below, preferably by intramuscular injection or by implantation. Such dosage forms are designed to release from about 0.5 mcg to about 50 mcg per kilogram body weight per day.

It is often desirable to administer a peptide of formula 1 or 1a continuously over prolonged periods of time in long-acting, slow-release, or depot dosage forms. Such dosage forms may either contain a pharmaceutically acceptable salt of the peptide having a low degree of solubility in body fluids, for example one of those salts described below, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example zinc hydroxide, and may be administered in suspension in a pharmaceutically acceptable liquid vehicle; or the peptide may be formulated in gels or suspensions with a protective non-antigenic hydrolcolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton, Pennsylvania, 1970. Long-acting, slow-release preparations of the peptide of formulae 1 or 1a may also be obtained by microencapsulation in a pharmaceutically acceptable coating, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York 1967, pp 436 – 456. Such formulations, as well as suspensions of salts of the agent which are only sparingly soluble in body fluids, for example salts with pamoic acid or tannic acid, are designed to release from about 5.0 mcg to about 100 mcg of the active compound per kilogram body weight per day, and are preferably administered by intramuscular injection. Alternatively, some of the solid dosage forms listed above, for example certain sparingly water-soluble salts or dispersions in or adsorbates on solid carriers of salts of the agent, for example dispersions in a neutral hydrogel of a polymer of ethylene glycol methacrylate or similar monomers crosslinked as described in U.S. Pat. No. 3,551,556 may also be formulated in the form of pellets releasing about the same amounts as shown above and may be implanted subcutaneously or intramuscularly.

PROCESS

For convenience and clarity in the following discussion the individual peptide unit (i.e., amino acid) is designated sometimes by a number which refers to the position in which the particular amino acid appears in the sequence of the amino acids as illustrated in the formula 1.

The process of this invention is carrier out in the following manner.

With reference to the tripeptide fragment 1–3, the tripeptide is prepared by reacting a protected activated ester of D-threonine, preferably

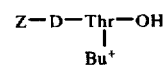

with a lower alkyl ester of D-phenylalanine, preferably H-D-Phe-OMe, to obtain the corresponding lower alkyl ester of the dipeptide

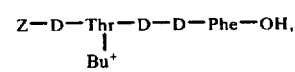

which after removal the terminal protecting group (Z) using hydrogen in the presence of a noble metal catalyst yields the corresponding lower alkyl ester of

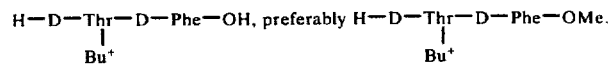

In turn the latter compound is reacted with a protected activated ester of D-serine, preferably the benzotriozolyl ester to obtain the corresponding lower alkyl ester of

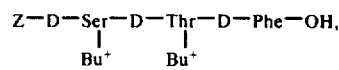

preferably

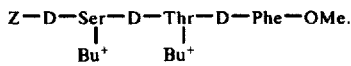

Subsequent removal of the terminal amino protecting group of the latter compound using hydrogen in the presence of a noble metal catalyst yields the corresponding lower alkyl ester of

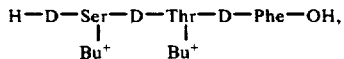

preferably

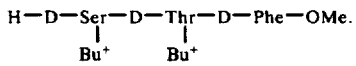

Condensation of said last-named compound with a protected activated ester of thiopropionic acid, preferably the benzotriazolyl ester, gives the corresponding protected lower alkyl ester of

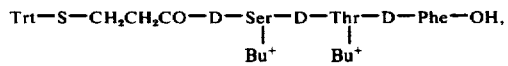

preferably

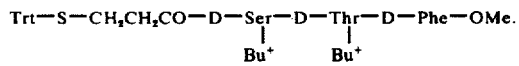

The latter compound is treated with hydrazine hydrate to obtain the hydrazide of the tripeptide fragment 1–3 of formula

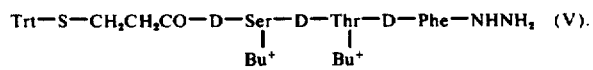

In a preferred embodiment of the preparation of the above tripeptide fragment 1–3, mixture of substantially equimolar amouns of

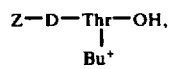

prepared from D-threonine in the same manner as described for the corresponding L-isomer by E. Schröder, Justus Liebigs' Ann. Chem. 670, 127 (1963) and H-D-Phe-OMe.HCl, prepared from D-phenylalanine in the same manner as described for the L-isomer by F. Bergel, J. M. Johnson, and R. Wade, J. Chem. Soc., 3802 (1962), in an inert organic solvent, preferably DMF or THF, at −20° to 10° C, preferably at 0° C, is treated with a molar excess, preferably with 1.1 to 1.3 molar equivalents of a strong organic base, preferably N-ethyl-morpholine, to pH 7–8. A molar excess, preferably 1.1 to 1.3 molar equivalents, of 1-hydroxybenzotriazole is added followed by the dropwise addition of a substantially molar equivalent of DCC (1.0 to 1.3 molar equivalents) in an inert organic solvent, preferably DMF or THF. The mixture is kept at −20° to 10° C, preferably at 0° C from 30 minutes to 2 hours and then at 20° to 30° C for an additional hour, filtered, and the filtrate evaporated. The residue is taken up in a substantially water-immiscible organic solvent, preferably diethyl ether, washed, dried, and evaporated. The residue is taken up in a mixture of a lower alkyl ester of a lower alkanoic acid, preferably ethyl acetate, and a hydrocarbon, preferably hexane, and is purified by chromatography on silica gel to yield the dipeptide of formula

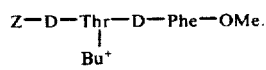

Said last-named compound is then subjected to hydrogenation in the presence of a noble metal catalyst, preferably 5% palladium on charcoal (5% Pd/C), and of an equimolar amount of pyridine hydrochloride or of an excess of acetic acid. Methanol, ethanol, acetic acid, or mixtures thereof are convenient solvents for this hydrogenation. In this manner the terminal amino protecting group (Z) of the above dipeptide is removed to give the corresponding dipeptide of formula

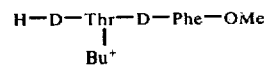

as its acetic acid or hydrochloric acid addition salt. Said last-named compound and a substantially equimolar amount of

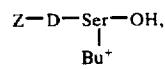

prepared as described for the L-isomer by E. Schröder, Justus Liebigs' Ann. Chem., 670, 127 (1963), in an inert organic solvent, preferably DMF or THF, at −20° to 10° C, preferably at 0° C, is treated with a molar excess, preferably 1.1 to 1.3 molar equivalents, of a strong organic base, preferably N-ethylmorpholine, to pH 7 − 8. A substantially equimolar amount of 1-hydroxybenzotriazole is added followed by the addition of a substantially molar equivalent of DCC (1.0 to 1.3 molar equivalents) in an inert organic solvent, preferably DMF or THF, and the mixture is cooled to −20° to 10° C, preferably to 0° C. The mixture is kept at −20° to 10° C, preferably at 0° C from 30 minutes to two hours and then at 20° to 30° C for an additional hour, filtered, and the filtrate is evaporated. The residue is taken up in a substantially water-immiscible organic solvent, preferably diethyl ether, washed, dried, and evaporated. The residue is taken up in a mixture of a lower alkyl ester of a lower alkanoic acid, preferably ethyl acetate, and a hydrocarbon, preferably hexane, and is purified by chromatography on silica gel to yield

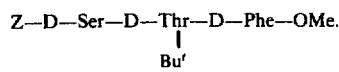

Said last-named compound is dissolved in a lower alkanol or a lower alkanoic acid or a mixture thereof, preferably in acetic, a noble metal catalyst, preferably 5% Pd/C, is added and the mixture is agitated in an atmosphere of hydrogen at room temperature for 10–30 hours, preferably for about 20 hour, until substantially one molar equivalent of hydrogen has been taken up. Filtration of the catalyst and evaporation of the filtrate yields the tripeptide of formula

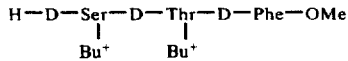

as the acetic acid addition salt. Said last-named compound is dissolved in an inert organic solvent, preferably DMF or THF, at −20° to 10° C, preferably at 0° C, and treated with a molar excess, preferably 1.1 to 1.3 molar equivalents, of a strong organic base, preferably N-ethylmorpholine, to pH 7 – 8. A substantially equimolar amount of 3-tritylthiopropionic acid, prepared as described by E. Billman and N. V. Due, Bull. Soc. Chim. Fr., 35, 384 (1924), in an inert organic solvent, preferably DMF or THF, is added followed by the addition of a substantially molar equivalent of 1-hydroxybenzotriazole. A molar excess of DCC (1.1 to 1.3

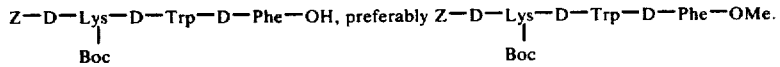

molar equivalents) in an inert organic solvent, preferably DMF or THF, is added and the mixture is kept at −20° to 10° C, preferably at 0° C from 30 minutes to 2 hours and then at 20° to 30° C for an additional hour, filtered, and the filtrate evaporated. The residue is taken up in a substantially water-immiscible organic solvent, preferably diethyl ether, the precipitate is removed by filtration, washed, dried, and evaporated. The residue is taken up in a mixture of a lower alkyl ester of a lower alkanoic acid, preferably ethyl acetate, an aromatic hydrocarbon, preferably benzene, and a strong organic base, preferably triethylamine, and is purified by chromatography on silica gel. Crystallization of the purified material yields

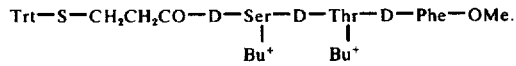

Said last-named compound is dissolved in an inert organic solvent, for example methanol, ethanol, DMF, preferably methanol, and the solution is treated with an excess of hydrazine hydrate, for example with 20 to 50 molar equivalents. The reaction mixture is kept at −20° to 10° C, preferably at 0° C, from 30 minutes to 2 hours and then at 20° to 30° C for 15 to 30 hours, preferably for 24 hours. Water is added, the resulting precipitate is collected by filtration and dried to yield the tripeptide fragment 1–3 of formula

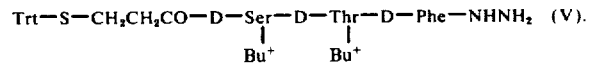

With reference to the tetrapeptide fragment 4–7, the tetrapeptide is prepared by reacting an amino protected D-tryptophane, preferably Z-D-Trp-OH, with a lower alkyl ester of D-phenylalanine, preferably H-D-Phe-OMe, to obtain an amino protected lower alkyl ester of the dipeptide H-D-Trp-D-Phe-OH, preferably Z-D-Trp-D-Phe-OMe, which after removal of the terminal protecting group (Z) using hydrogen in the presence of a noble metal catalyst yields the corresponding lower alkyl ester of H-D-Trp-D-Phe-OH, preferably H-D-Trp-D-Phe-OMe. In turn, the latter compound is reacted with an activated ester of

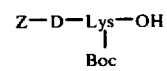

to give the corresponding lower alkyl ester of

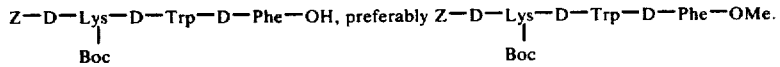

Subsequent removal of the terminal amino protecting group of the latter compound (Z) using hydrogen in the presence of a noble metal catalyst gives the corresponding lower alkyl ester of

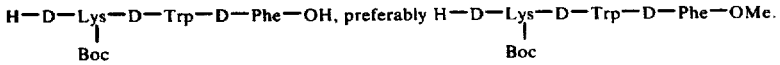

Condensation of the last-named compound with an activated ester

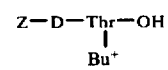

yields the corresponding lower akyl ester of

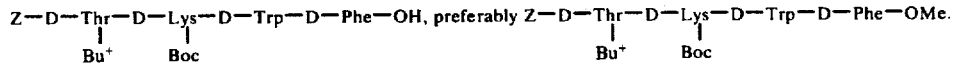

The latter compound is treated with hydrazine hydrate to obtain the tetrapeptide fragment 4–7 of formula

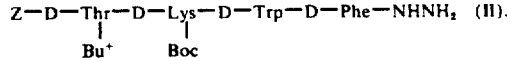

In a preferred embodiment of the preparation of the above tetrapeptide fragment 4–7, substantially equimolar amounts of Z-D-Trp-OH, prepared as described for the L-isomer by E. Klieger, E. Schroder, and H. Gibian, Justus Liebigs' Ann. Chem., 640, 157 (1961), and H-D-Phe-OMe.HCl (see F. Bergel et al. cited above) with an excess, preferably 1.5 to 2.5 molar equivalents, of 1-hydroxybenzotriazole, in an inert organic solvent, preferably DMF, at −20° to 10° C, preferably 0° C, is treated with an excess, preferably 1.1 to 1.3 molar equivalents, of an organic base, preferably N-ethylmorpholine, to pH 7 – 8. A substantially equimolar amount of DCC in an inert organic solvent, preferably DMF, at −10° to 10° C, is added dropwise. The mixture is kept at −20° to 10° C for an additional hour, cooled to −10° to 10° C, filtered, and the filtrate evaporated. The residue is taken up in a substantially water-immiscible solvent, preferably ethyl acetate, washed, dried and evaporated. The residue is taken up in a mixture of a halogenated hydrocarbon solvent, preferably chloroform, and a lower alkanol, preferably methanol. The solution is passed through a column of silica gel. Evaporation of the eluate and crystallization of the residue yields the dipeptide fragment 6–7 of formula Z-D-Trp-D-Phe-OMe. Said last-named compound is then subjected to hydrogenation in the presence of a noble metal catalyst, preferably 5% Pd/C. Methanol, ethanol, acetic acid, or mixtures thereof are convenient solvents for this hydrogenation. When acetic acid is used the product will be isolated as the acetic acid addition salt. Filtration of the catalyst, and evaporation of the filtrate yields the dipeptide fragment 6–7 of formula H-D-Trp-D-Phe-OMe. Said last-named compound in an inert organic solvent, preferably DMF, at −20° to 10° C, preferably 0° C, is treated with an excess, preferably 1.1 to 1.3 molar equivalents, of a strong organic base, preferably N-ethylmorpholine, to pH 7 – 8, the mixture is then treated with a substantially molar equivalent of a protected activated ester of D-lysine, preferably

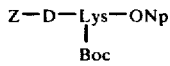

prepared in the same manner from D-lysine as described for the L-isomer by E. Sandrin and R. A. Boissonnas, Helv. Chim. Acta., 46, 1637 (1963). The solution is stirred at about 0° C for 30 minutes to two hours, at 20° − 30° C for two to four days and evaporated. The residue is taken up in a substantially water-immiscible solvent, preferably ethyl acetate, washed, dried, and evaporated. The residue is taken up in a halogenated hydrocarbon solvent, preferably chloroform, a lower alkanol, preferably methanol, and a strong organic base, preferably pyridine. The solution is passed through silica gel. After evaporation of the eluate the residue is crystallized to yield the tripeptide fragment 5–7 of formula

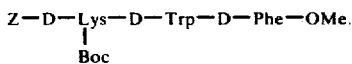

Said last-named compound is then subjected to hydrogenation in the presence of a noble metal catalyst, preferably 5% Pd/C. Methanol, ethanol, acetic acid, or mixtures thereof are convenient solvents for this hydrogenation, when acetic acid is used the product will be isolated as the acetic acid addition salt. Filtration of the catalyst, and evaporation of the filtrate yields the tripeptide fragment 5–7 of formula

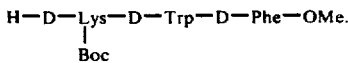

Said last-named compound, substantially equimolar amount of a protected D-threonine, preferably

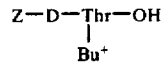

(see E. Schröder cited above), and about one to two molar equivalents of 1-hydroxybenzotriazole in an inert organic solvent, preferably DMF, at −20° to 10° C, preferably 0° C, is treated with an excess, preferably 1.1 to 1.3 molar equivalents, of a strong organic base, preferably N-ethylmorpholine, to pH 7 – 8. A substantially equimolar amount of DCC in an inert solvent, preferably DMF, at about 0° C is slowly added dropwise. The mixture is stirred at about 0° C for 30 minutes to two hours, at 20° – 30° C for one to two hours, filtered, and evaporated. The residue is taken up in a halogenated hydrocarbon solvent, preferably chloroform, and a lower alkanol, preferably methanol. The solution is passed through a column of silica gel. Evaporation of the eluate and crystallization of the residue yields the tetrapeptide fragment 4–7 of formula

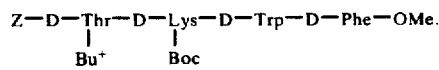

Said last-named compound is dissolved in an inert organic solvent, for example methanol, ethanol, or DMF, preferably DMF. The solution is treated with an excess of hydrazine hydrate, for example 20 to 50 molar equivalents, and is kept at −20° to 10° C, preferably at 0° C, for one and a half to three hours, preferably two hours. Water is added; the precipitate is collected by filtration, dried, and crystallized to yield the tetrapeptide fragment 4–7 of formula

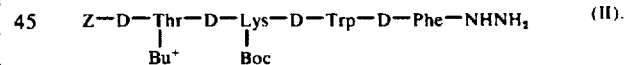

With reference to the tripeptide fragment 8–10, the tripeptide is prepared by reacting a protected activated ester of D-asparagine, preferably Z-D-Asn-OTcp, with a lower alkyl ester of a protected D-lysine, preferably

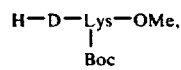

to obtain the corresponding protected lower alkyl ester of the dipeptide D-asparaginyl-D-lysine, preferably

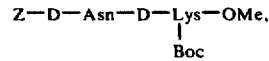

which after removal of the terminal amino protecting group (Z) using hydrogen in the presence of a noble metal catalyst gives the corresponding lower alkyl ester of

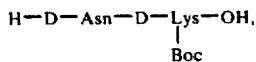

preferably

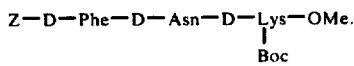

Subsequent removal of the terminal amino protecting group of the latter compound (Z) using hydrogen in the presence of a noble metal catalyst gives the corresponding lower alkyl ester of

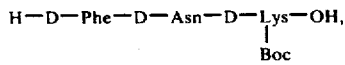

preferably the tripeptide fragment 8–10 of formula

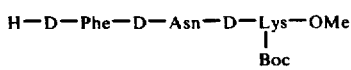 (III).

In a preferred embodiment of the preparation of the tripeptide fragment 8–10, substantially equimolar amounts of Z-D-Asn-OTcp, prepared from D-asparagine in the same manner as described for the corresponding L-isomer by J. Beacham, G. Dupuis, F. M. Finn, H. T. Storey, C. Yanaihara, N. Yanaihara, and K. Hofmann, J. Amer. Chem. Soc., 93, 5526 (1971), and

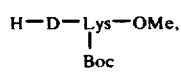

prepared from D-lysine in the same manner as described for the corresponding L-isomer by R. Schwyzer and W. Rittel, Helv. Chim. Acta, 44, 159 (1961), in an inert organic solvent, preferably DMF, at −20° to 10° C, preferably 0° C, is treated with a substantially molar equivalent of an organic base, preferably N-ethylmorpholine and stirred at −20° to 10° C, preferably 0° C, for two to four hours, and then at 20° to 30° C for 15 to 30 hours. The solution is evaporated, the residue is triturated with an alkyl ether, preferably diethyl ether and dried to yield the dipeptide fragment 9–10 of formula

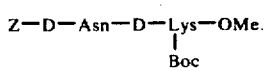

Said last-named compound is then subjected to hydrogenation in the presence of a noble metal catalyst, preferably 5% Pd/C. Methanol, ethanol, acetic acid or mixtures thereof are convenient solvents for this hydrogenation. The catalyst is removed by filtration, the filtrate is treated with a substantially equimolar amount of a mineral acid, preferably hydrochloric acid, and evaporated to yield the dipeptide fragment 9–10 of formula

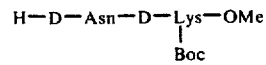

as the hydrochloric acid addition salt. Said last-named compound and a substantially equimolar amount of Z-D-Phe-OTcp, prepared from D-phenylalanine in the same manner described for the corresponding L-isomer by J. Pless and R. A. Boissonnas, Helv. Chim. Acta., 46 1609 (1963), in an inert organic solvent, preferably DMF or THF, at −20° to 10° C, preferably 0° C, is treated with an excess, preferably 1.1 to 1.3 molar equivalents, of an organic base, preferably N-ethylmorpholine. The solution is stirred at about 0° C for 20 to 30 hours. The precipitate is collected by filtration and crystallized to obtain the tripeptide fragment 8–10 of formula

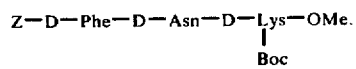

The latter compound is subjected to hydrogenation in the presence of a noble metal catalyst, preferably 5% Pd/C. Methanol, ethanol, acetic acid, or mixtures thereof are convenient solvents for this hydrogenation, when acetic acid is used the product will be isolated as the acetic acid addition salt. The catalyst is removed by filtration, the filtrate evaporated, the residue taken up in an aromatic hydrocarbon, preferably benzene, and evaporated to obtain the tripeptide fragment 8–10 of formula

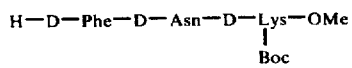 (III).

With reference to the fragment

 (VII)

in which R is $CONHCH_2CONHCH_2CH_3$, i.e. the fragment VIIb alternatively written as

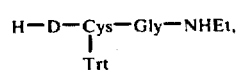

said fragment is prepared by reacting a protected lower alkyl ester of the dipeptide D-cysteinyl-glycine, preferably

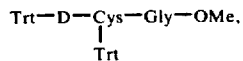

with ethylamine, to obtain the correspondingly protected ethylamide of the dipeptide D-cysteinyl-glycine, preferably

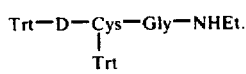

Removal of the terminal amino protecting group (Trt) using mildly acidic conditions, preferably a mixture of water and acetic acid or formic acid yields the corresponding addition salt of the fragment

in which R is CONHCH$_2$CONHCH$_2$CH$_3$,

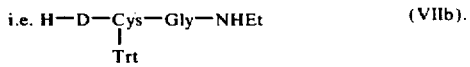

In a preferred embodiment of the preparation of the fragment (VII) in which R is CONHCH$_2$CONHCH$_2$CH$_3$, the dipeptide

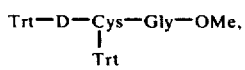

prepared from D-cysteine in the same manner as described for the corresponding L-isomer by G. Amiard, Bull. Soc. Chim. (Fr.), 1956, 698, is treated with a molar excess, preferably 50 – 200 molar equivalents, of ethylamine at −15° to 15° C, preferably 5° C, for 20 to 30 hours. The solution is evaporated, and the residue is dissolved in a solution of a lower alkyl ester of a lower alkanoic acid, preferably ethyl acetate, and an aromatic hydrocarbon, preferably benzene, and purified by chromatography on silica gel to obtain the dipeptide of formula

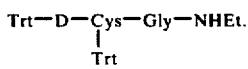

Said last-named compound is subjected to mildly acidic conditions, preferably 70 to 90% acetic acid at 30° to 50° C, preferably 45° C, for 10 to 20 minutes, preferably 15 minutes. Water is added, the mixture is filtered, the filtrate is treated with a substantially molar equivalent of a mineral acid, preferably hydrochloric acid, to obtain the fragment

in which R is CONHCH$_2$CONHCH$_2$CH$_3$ alternatively written

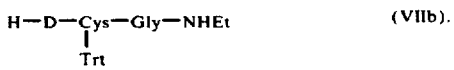

The heptapeptide fragment 4–10 is conveniently prepared by coupling the fragment 4–7 and the fragment 8–10 according to the azide coupling method in the following manner. A solution of the tetrapeptide fragment 4–7 of formula

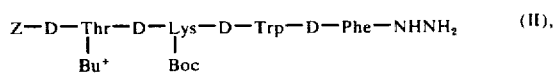

obtained as described above, in an inert anhydrous organic solvent, preferably DMF, is cooled to a temperature of from about −30° C to about −10° C and mixed with a solution of about two to five molar equivalents, preferably three molar equivalents, of a mineral acid, preferably hydrogen chloride, in an inert anhydrous organic solvent, preferably ethyl acetate. An organic nitrite, preferably t-butyl nitrite or isoamyl nitrite in a substantially equimolar amount is added with stirring. The solution is stirred for 10–30 minutes, preferably for about 15 minutes, at a temperature of from about −20° C to about −10° C. Keeping the solution at a temperature of from about −30° C to about −10° C, a solution of a substantially equimolar amount of the tripeptide fragment 8–10 of formula

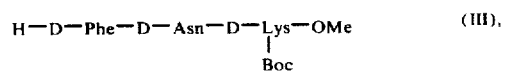

preferably as the acetic acid addition salt obtained as described above, and of about three to five molar equivalents, preferably about 3.5 molar equivalents, of an organic base, preferably N-ethyldiisopropylamine, in an inert anhydrous organic solvent, preferably DMF, is added slowly with stirring. The mixture is stirred for 30 – 60 minutes at about −20° C to about −10° C, then at about 20° to 30° C for 20 to 30 hours. The solution is evaporated and the residue is triturated with cold aqueous citric acid (0.5 to 2N), water and dried. The residue is taken up in a mixture of a halogenated hydrocarbon, preferably chloroform, and a lower alkanol, preferably methanol, and purified by chromatography on silica gel. The solvent is evaporated and the residue crystallized to yield the heptapeptide fragment 4–10 of formula

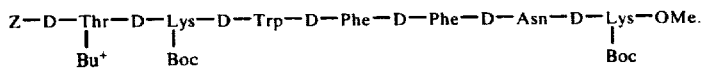

Said last-named compound is subjected to hydrogenation in the presence of a noble metal catalyst, preferably 5% Pd/C. Methanol, ethanol, acetic acid, or mixtures thereof are suitable solvents for this hydrogenation, and when acetic acid is used the product is isolated as the acetic acid addition salt. The catalyst is removed by filtration; the filtrate evaporated, the residue taken up in an aromatic hydrocarbon, preferably benzene, evaporated, and dried over strong alkali, preferably potassium hydroxide or sodium hydroxide, to obtain the heptapeptide fragment 4–10 of formula

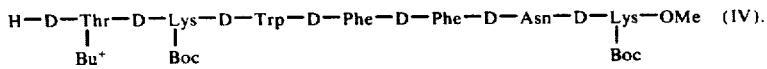

The decapeptide fragment 1–10 is conveniently prepared by coupling the fragment 1–3 and the fragment 4–10 according to the azide coupling method in the following manner. A solution of the tripeptide fragment 1–3 of formula

obtained as described above, in an inert anhydrous solvent, preferably DMF, is cooled to a temperature of from about −30° C to about −10° C and mixed with a solution of about two to five molar equivalents, preferably three molar equivalents, of a strong mineral acid, preferably hydrogen chloride, in an anhydrous organic solvent, preferably ethyl acetate. An organic nitrite, preferably t-butyl nitrite or isoamyl nitrite, in a substantially equimolar amount, is added with stirring. The solution is stirred for 10 – 30 minutes, preferably for about 15 minutes, at a temperature of from about −20° C to about −10° C. Keeping the solution at a temperature of from about −30° C to about −10° C, a solution of a substantially equimolar amount of the heptapeptide fragment 4–10 of formula DMF, preferably DMF, and treated with an excess of hydrazine hydrate, for example 20 to 50 molar equivalents. The mixture is kept at −20° to 10° C, preferably 0° C, for 15 to 45 minutes and at 20° C to 30° C, for 20 to 30 hours. Water is added, the precipitate is collected by filtration, washed with water, and dried to yield the decapeptide fragment 1–10 of formula

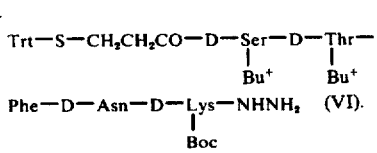

The linear peptide VIII is conveniently prepared by coupling the fragment 1–10 (VI) and the fragment (VII) according to the azide coupling method in the following manner. A solution of the decapeptide fragment 1–10 (VI), obtained as described above, is taken up in an inert anhydrous organic solvent, preferably a mixture of DMF and DMSO, cooled to a temperature of from about −30° C to about −10° C and mixed with a solution of about two to five molar equivalents, preferably three molar equivalents of a mineral acid, preferably hydrogen chloride, in an anhydrous organic solvent, preferably ethyl acetate. A substantially equimolar amount of an organic nitrite, preferably t-butyl nitrite or isoamyl nitrite, is added, and the solution is stirred for 10–30 minutes, preferably for about 15 minutes, at a temperature of from about −20° C to about −10° C. Keeping the stirred solution at a temperature of from about −30° C to about −10° C, a solution of a

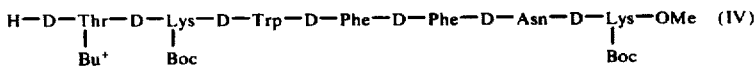

obtained as described above, and of about about three to five molar equivalents, preferably about 3.5 molar equivalents, of an organic base, preferably N-ethyldiisopropylamine, in an inert anhydrous organic solvent, preferably DMF, is slowly added with stirring. Stirring of the resulting mixture is continued for 30 – 60 minutes at about −20° C to about −10° C, then at about 20° to 30° C for 20 to 30 hours. The solution is evaporated, the residue is triturated with cold aqueous citric acid (0.5 to 2N), water and dried. The residue is taken up in a mixture of a halogenated hydrocarbon, preferably chloroform, and a lower akanol, preferably methanol, purified by chromatography on silica gel and crystallized to yield the decapeptide fragment 1–10 of formula

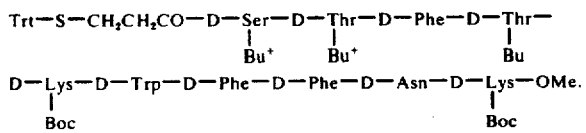

Said last-named compound is taken up in an inert organic solvent, for example methanol, ethanol, or substantially equimolar amount of the fragment

in which R is CONHCH$_2$CONHCH$_2$CH$_3$(VIIb) obtained as described above or the fragment

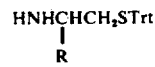

in which R is hydrogen (VIIa) [described by F. I. Carroll et al., J. Org. Chem. 30, 36 (1965)], and of about three to five molar equivalents, preferably about 3.5 molar equivalents, of an organic base, preferably N- ethyldiisopropylamine, in an inert anhydrous organic solvent, preferably DMF, is added slowly. Stirring of the resulting mixture is continued for 45 – 75 minutes at about −20° C to about −10° C, then at about 20° to 30° C for 20 to 30 hours. Evaporation of the solution, trituration of the residue with cold aqueous citric acid (0.5 to 2N), water, methanol, and drying yields the corresponding linear protected peptide of formula (VIII)

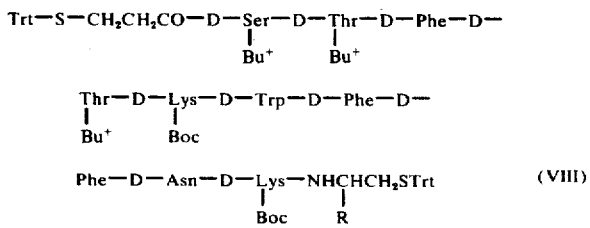

in which R is as defined herein.

The conversion of the above linear protected peptide, obtained as described above, to the compound of formula I is accomplished conveniently and efficiently by subjecting the linear protected peptide to the action of iodine, preferably in the presence of a lower alkanol or a lower alkanoic acid whereby simultaneous removal of the sulfhydryl protecting groups, i.e. Trt, and formation of the disulfide bridge occurs to give the corresponding cyclic disulfide of formula IX

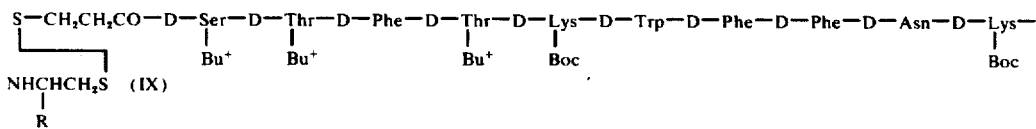

in which R is as defined herein, subsequent treatment of the latter compound under moderately acidic conditions removes the remaining protecting groups (i.e. Boc and Bu⁺) to give the corresponding compound of formula I.

In a preferred embodiment of the above transformation, the linear protected peptide (VIII) is dissolved in a lower alkanol or a lower alkanoic acid, preferably acetic acid, and added to an excess of iodine (5 to 25 molar equivalents, preferably 10 molar equivalents) dissolved in a lower alkanol or a lower alkanoic acid, preferably methanol, at a concentration of about 2 –5% iodine. The time and temperature of this reaction is not critical; however, it is desirable to keep the reaction between 0° and 30° C by regulating the addition to the iodine solution or by cooling of the reaction mixture, or by a combination of both. Under these conditions the addition usually takes 30 to 60 minutes. After the addition the mixture is stirred at 20° to 30° C for 30 to 120 minutes, preferably 60 minutes. Thereafter the mixture is cooled to about 0° C and an excess of a mild reducing agent, preferably sodium thiosulfate in aqueous solution is added. The mixture is concentrated and the residue is suspended in water. Collection of the solid material affords the desired correspondng cyclic disulfide of formula IX.

Alternatively, the linear protected peptide (VII) is converted to the abovementioned corresponding cyclic disulfide by the method of R. G. Hiskey and R. L. Smith, J. Amer. Chem. Soc., 90, 2677 (1968) using thiocyanogen.

Again alternatively, the cyclic disulfide (IX) is also obtained by selectively removing the sulfhydryl protecting groups of the above linear protected peptide (VIII) by the action of a mercuric or silver salt, for example, mercuric acetate, mercuric chloride, silver acetate or silver nitrate, in an inert organic solvent, for example DMF or acetic acid, according to known methods; for example, see B. Kamber, and N. Rittel, Helv. Chem. Acta, 52, 1074 (1964), L. Zervas, et al., J. Amer. Chem. Soc., 87, 4922 (1965) and R. G. Denkewalter et al., J. Amer. Chem. Soc., 91, 502 (1969). The mercuric or disilver salt thus obtained is then converted to the corresponding free disulfhydryl derivative (X)

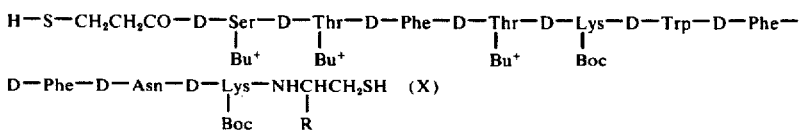

in which R is as defined herein by treatment with hydrogen sulfide, see L. Zervas, et al., cited above. The latter derivative is then converted to the aforementioned cyclic disulfide (IX) by a mild oxidizing agent selected from the group consisting of iodine according to the method described hereinbefore, oxygen according to the method of J. Rivier, et al., C.R. Acad. Sci. Ser. D, 276, 2737 (1973), 1,2-diiodoethane according to the method of F. Weygand and G. Zumach, Z. Naturforsch. 17b, 807 (1962), and sodium or potassium ferricyanide according to the method of D. Jarvis, et al., J. Amer. Chem. Soc., 83, 4780 (1961).

Finally, the aforementioned cyclic disulfide of formula IX is transformed into the corresponding cyclic peptide of formula I, by subjecting the former to moderately acidic conditions whereby the remaining protecting groups of the cyclic disulfide (IX) are removed. Generally this step is carried out by treating the cyclic disulfide (IX) with 50 – 100% trifluoroacetic acid or with an aqueous solution containing a mineral acid 0° to 20° C for 10 to about 60 minutes. Examples of such mineral acids are 10 to 20% aqueous sulfuric acid, 10 % phosphoric acid, 10 – 30% hydrobromic acid and 10 to 36% hydrochloric acid. An extremely useful acid is concentrated hydrochloric acid. Preferred conditions for the present step include dissolving the cyclic disulfide in a minimum of concentrated hydrochloric acid cooled to 0° C and stirring the mixture at 0° C for 5 to 10 minutes under a nitrogen atmosphere. Thereafter glacial acetic acid (10 X vols.) is added, the solution is cooled to about −70° C and lyophilized to give the corresponding cyclic peptide of formula I. The latter product is purified further by ion exchange chromatography using a carboxymethylcellulose cation exchanger and ammonium acetate as the eluant. In the latter case the product is obtained in the form of its acid addition salt with acetic acid. Alternatively, the product is purified by partition chromatography on a chemically modified cross-linked dextran, for example Sephadex LH-20 or Sephadex G-25, using methanol or acetic acid, respectively, as the eluting solvent. In the case where Sephadex LH-20 and methanol as the eluting solvent is employed, the product is obtained in the form of its hydrochloric acid addition salt. In the case where Sephadex G-25 and acetic acid is employed, the product is obtained in the form of its acetic acid addition salt. Repeated lyophilization from water of the product in the form of its acetic acid addition salt yields the substantialy pure cyclic peptide of formula I in which R is as defined herein, in the form of the free base.

The linear reduced form of the peptide of formula Ia is obtained by removal of the protecting groups from the aforementioned linear protected peptide of formula (VIII)

in which R is as defined herein from the aforementioned disulfhydryl derivative of formula (X)

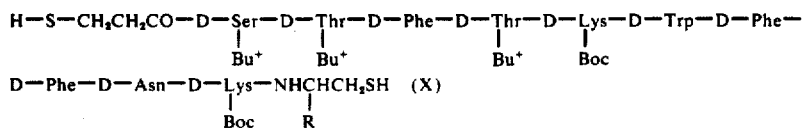

in which R is as defined herein under moderately acidic conditions. Preferred conditions for this deprotection step comprises dissolving the linear protected peptide (VIII) or the disulfhydryl derivative (X) in concentrated hydrochloric acid at 0° to 5° C in an inert atmosphere, for example, nitrogen or argon. The mixture is kept at this temperature for five to ten minutes. Subsequent isolation of the linear reduced form is accomplished in the same manner as described previously for the isolation of the cyclic peptide of formula I.

Also, the linear reduced form (Ia) is obtained directly by reduction of the cyclic peptide of formula I. Reduction with dithiothreitol according to the method of W. W. Cleland, Biochem. 3, 480 (1964) is preferred, although other agents known to be effective for the reduction of cyclic disulfides to the corresponding disulfhydryl derivative are applicable, for example, sodium bisulfite followed by hydrolysis of the intermediate dithiosulfate derivative.

Finally it will be apparent to those skilled in the art that: equivalent amino, hydroxy or thiol protecting groups, equivalent methods of coupling peptide fragments, and equivalent methods for removal of amino, hydroxy or thiol protecting groups, other than those disclosed herein could be used in the embodiments of this invention without departing from the scope and spirit of the invention. Such apparent alterations are intended to be included within the scope of this invention.

The following flow diagrams and examples illustrate further this invention.

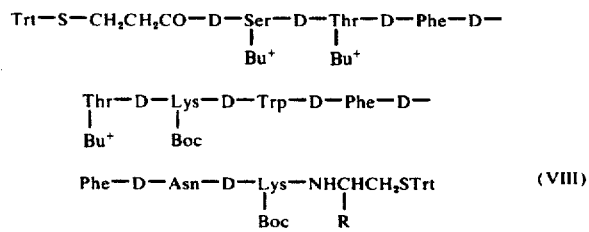

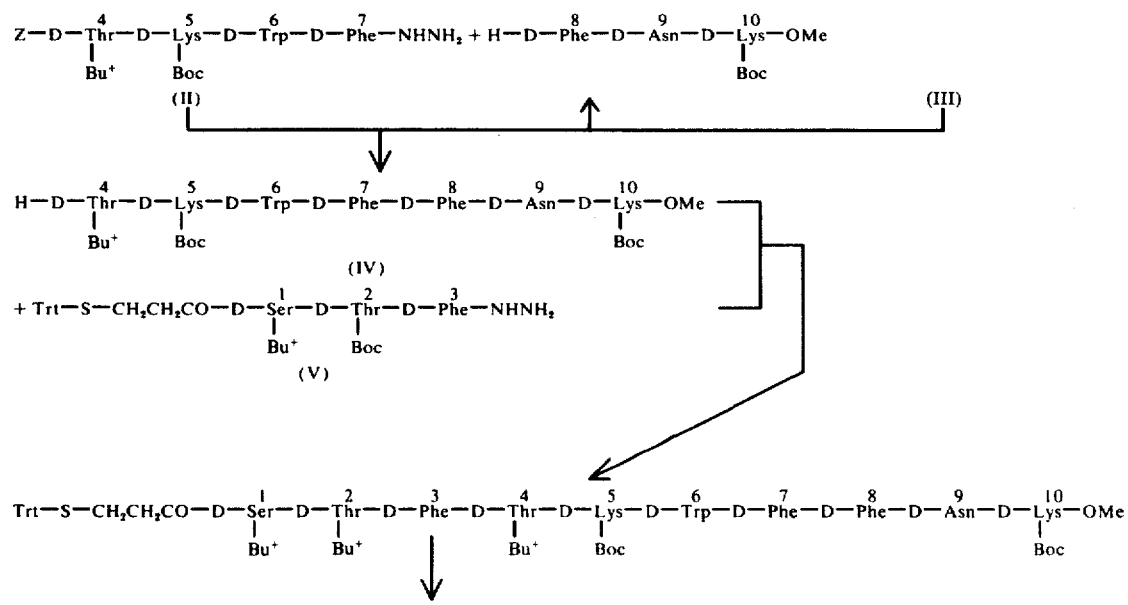

-continued
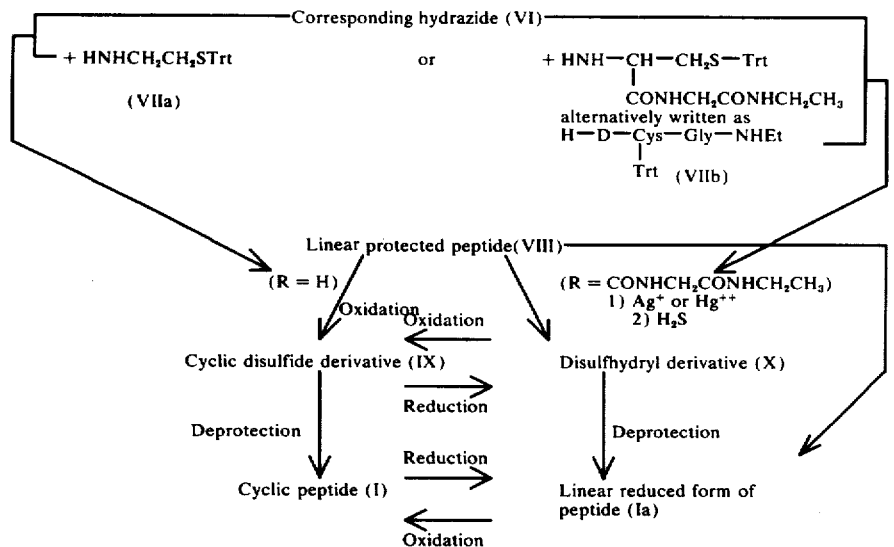
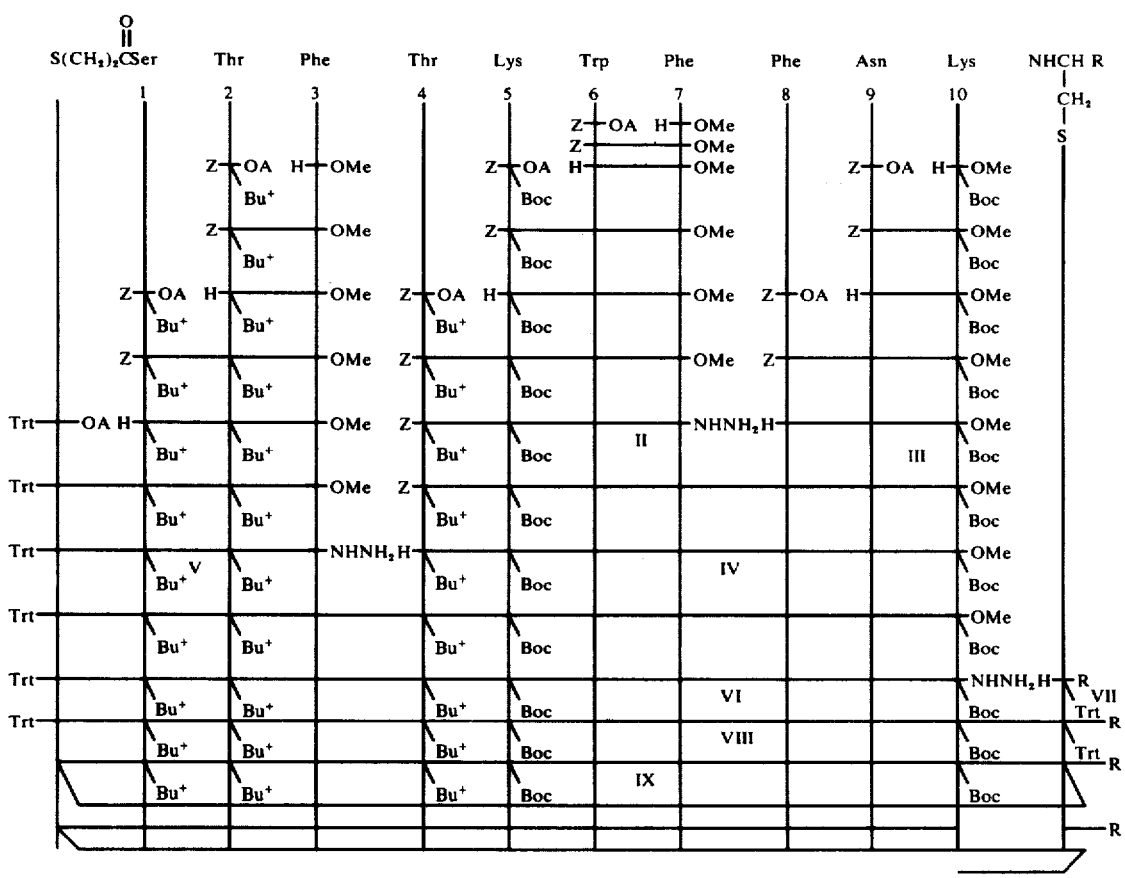
A = O-(carboxyl-activating group); R = H or CONHCH₂CONHCH₂CH₃
EXAMPLE 1
Benzyloxycarbonyl-(O-t-butyl)-D-threonyl-D-phenylalanine Methyl Ester (Z—D—Thr—D—Phe—OMe)
         |
        Bu⁺
A mixture of
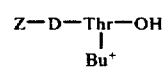
(3.1 g, 10 mmoles) and H-D-Phe-OMe.HCl (2.16 g, 10 mmoles) in THF (15 ml) is cooled to 0° C and N-ethylmorpholine (1.8 ml) added to attain a pH of 7 - 8. 1-Hydroxybenzotriazole (1.4 g, 10.3 mmoles) is added followed by dropwise addition of DCC (2.1 g, 10 mmoles) in THF (20 ml). The mixture is stirred at 0° C for 45 min and at room temperature for 1 hr. After filtration, the filtrate is concentrated under reduced pressure and the residue dissolved in ether. After filtration of the precipitate, the filtrate is washed with saturated NaHCO₃ solution, saturated NaCl solution, 5% aqueous citric acid solution, and saturated NaCl solution. The ether solution is dried over Na₂SO₄ and evaporated under reduced pressure. The residue is subjected to chromatography on silica gel (200 g) using 25% EtOAc in hexane. Evaporation of the solvent under reduced pressure gives the title compound as an oil, $[\alpha]_D^{25} = -25.1°$ (c = 1, DMF), nmr (CDCl₃) δ 1.08 (d,J = 6.5Hz, 3H), 1.15 (s, 9H), 3.70 (s, 3H), 5.18 (s, 2H), 7.35 (m, 10H).

EXAMPLE 2

Benzyloxycarbonyl-(O-t-butyl)-D-seryl-(O-t-butyl)-D-threonyl-D-phenyl-alanine Methyl Ester (Z—D—Ser—D—Thr—

D—Phe—OMe)   Bu⁺   Bu⁺

Z—D—Thr—D—Phe—OMe
       |
       Bu⁺

(7.5 g, 15.9 mmoles, described in Example 1) dissolved in MeOH (90 ml) containing pyridine hydrochloride (1.83 g, 15.9 mmoles) is hydrogenated with 5% Pd/C as a catalyst. The mixture is filtered and the filtrate taken to dryness under reduced pressure to give H-D-Thr-D-Phe-OMe.HCl. The above product and Z-D-Ser-OH (4.67 g, 15.9 mmoles) are dissolved in dry THF (45 ml), cooled to 0° C and 2.7 ml N-ethylmorpholine is added. 1-Hydroxybenzotriazole (2.16 g, 15.9 mmoles) is added followed by a cold (0° C) solution of DCC (3.27 g, 15.9 mmoles) in THF (30 ml). The mixture is stirred for 45 min at 0° C and then 1 hr at room temperature. After filtration, the THF is removed under reduced pressure, the residue taken up in ether and filtered. The filtrate is washed with saturated NaHCO₃ solution, saturared NaCl solution, ice-cold 5% citric acid solution, saturated NaCl solution, saturated NaHCO₃ solution and saturated NaCl solution. The residue (9.2 g) obtained after drying the ether layer with Na₂SO₄ and evaporating under reduced pressure is subjected to chromatography on a column of silica gel (200 g) using 30% EtOAc in hexane. The solvent is evaporated under reduced pressure to give the title compound as an oil, nmr (CDCl₃) δ 1.05 (d, J = 6.5 Hz, 3H), 1.18 (s, 18H), 3.75 (s, 3H), 5.18 (s, 2H), 7.4 (m, 10H).

EXAMPLE 3

(O-t-butyl)-D-seryl-(O-t-butyl)-D-threonyl-D-phenylalanine Methyl Ester

Acetate (H—D—Ser—D—Thr—D—Phe—OMe . CH₃CO₂H)
            |        |
            Bu⁺     Bu⁺

Z—D—Ser—D—Thr—D—Phe—OMe
     |       |
     Bu⁺    Bu⁺

(8.4 g, 13.6 mmoles, described in Example 2), dissolved in acetic acid (84 ml), is hydrogenated with 5% Pd/C as a catalyst for 20 hr. The mixture is filtered and the filtrate taken to dryness under reduced pressure to give the title compound as an oil: nmr (CDCl₃) δ 1.05 (d, J = 6.5 Hz, 3H), 1.19 (s, 18H), 2.06 (s, 3H), 3.76 (s, 3H).

EXAMPLE 4

N-[1-oxo-3-(trityl)thio]propyl-(O-t-butyl)-D-seryl-(O-t-butyl)-D-threonyl-D-phenylalanine Methyl Ester (Trt—S—CH₂CH₂CO—D—Ser—D—Thr—D—Phe—OMe)
              |         |
              Bu⁺      Bu⁺

A solution of

H—D—Ser—D—Thr—D—Phe—OMe . CH₃CO₂H
       |        |
       Bu⁺    Bu⁺

(13.6 mmoles, described in Example 3) in dry THF (25 ml) is cooled to 0° C and N-ethylmorpholine (1.7 ml) added until pH 7 is attained. A solution of 3-tritylthiopropionic acid (4.7 g, 13.6 mmoles) in THF (25 ml) is added followed by 1-hydroxybenzotriazole (1.8 g, 13.6 mmoles) and DCC (2.8 g, 13.6 mmoles) in THF (25 ml). The mixture is stirred at 0° C for 45 min and at room temperature for 2 hr. The precipitate is removed by filtration, and the filtrate is concentrated under reduced pressure. The residue is dissolved in ether and the precipitate removed by filtration. The filtrate is washed with saturated NaHCO₃ solution, saturated NaCl solution, cold 5% citric acid solution, saturated NaCl solution, saturated NaHCO₃ solution and saturated NaCl solution. The ether solution is dried over Na₂SO₄ and evaporated under reduced pressure. The residue is subjected to chromatograhy on a column of silica gel (220 g) using 30% EtOAc in benzene containing 0.2% triethylamine. After evaporation of the eluates, under reduced pressure the residue is crystallized from ether to give the title compound, mp 117–125° C$[\alpha]_D^{25} = 18.6°$ (c = 1, DMF).

EXAMPLE 5

N-[1-oxo-3-(trityl)thio]propyl-(O-t-butyl)-D-seryl-(O-t-butyl)-D-threonyl-D-phenyl-alanine Hydrazide (V, Trt—S—CH₂CH₂CO—D—Ser—D—Thr—D—Phe—NHNH₂)
               |         |
               Bu⁺      Bu⁺

Trt—S—CH₂CH₂CO—D—Ser—D—Thr—D—Phe—OMe
                     |       |
                     Bu⁺    Bu⁺

(2.025 g, described in Example 4) in MeOH (70 ml) and hydrazine hydrate (2 ml) is stirred at 0° C for 1 hr and at room temperature for 24 hr. The precipitate which is obtained upon addition of water is collected on a sintered glass filter and dried over phosphorus

EXAMPLE 6

Benzyloxycarbonyl-D-tryptophyl-D-phenylalanine Methyl Ester (Z-D-Trp-D-Phe-OMe)

A solution of Z-D-Trp-OH (3.62 g, 10.7 mmoles), H-D-Phe-Ome.HCl (2.3 g, 10.7 mmoles) and 1-hydroxybenzotriazole (2.89 g, 21.4 mmoles) in dry DMF (25 ml) is cooled to 0° C and N-ethylmorpholine (1.37 ml, 10.7 mmoles) is added. A cold (0° C) solution of DCC (2.27 g, 11 mmoles) in DMF (6 ml) is added dropwise and the reaction mixture is stirred for 1 hr at 0° C and 1 hr at room temperature. The reaction mixture is then cooled to 0° C, filtered, the filtrate evaporated under reduced pressure and taken upon in EtOAc. The EtOAc solution is washed with saturated NaHCO$_3$ solution, water, cold citric acid (2N), water, saturated NaHCO$_3$ solution and saturated NaCl solution, dried with MgSO$_4$, and evaporated under reduced pressure to afford the crude title product which is subjected to chromatography on a column of silica gel (500 g) with CHCl$_3$ containing MeOH (1%) as eluent. The eluates are evaporated under reduced pressure and the residue is crystallized from EtOAc-petroleum ether to give the title compound; mp 130° – 131° C, $[\alpha]_D^{25} = +34.1°$ (c = 1, DMF).

EXAMPLE 7

Benzyloxycarbonyl-N$^\epsilon$-t-butyloxycarbonyl-D-lysyl-D-tryptophyl-D-phenylalanine Methyl Ester (Z—D—Lys—D—Trp—D—Phe—OMe)
|
Boc A mixture of Z-D-Trp-D-Phe-Ome (2.00 g, 4.0 mmoles, described in Example 6) and 5% Pd/C (0.25 g) in acetic acid is stirred rapidly under an atmosphere of hydrogen. After completion of hydrogen uptake a stream of nitrogen is passed through the mixture for 15 min, the catalyst is removed by filtration, and the acetic acid is removed under reduced pressure. The residue is taken into benzene, evaporated under reduced pressure (twice), and dried under reduced pressure over KOH pellets to give H-D-Trp-D-Phe-OMe.CH$_3$CO$_2$H. The above product is dissolved in dry DMF (20 ml) and cooled to 0° C. N-ethylmorpholine (0.512 ml, 4 mmoles) is added, followed by

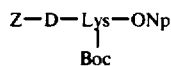

Z—D—Lys—ONp
|
Boc (2.00 g, 4 mmoles). The solution is stirred at 0° C for 30 min and for 3 days at room temperature. The solvent is evaporated under reduced pressure, the residue is taken into EtOAc and washed with cold saturated NaHCO$_3$ solution, water, cold citric acid (2N), water, saturated NaHCO$_3$ solution and saturated NaCl solution. The EtOAc solution is dried with MgSO$_4$ and evaporated under reduced pressure to afford the crude title product. After chromatography on a column of silica gel (300 g) with CHCl$_3$ containing MeOH (5%) and pyridine (0.1%) as eluent, the chromatographically pure product is triturated with ether, filtered, dried under reduced pressure, and crystallized from MeOH-CH$_2$Cl$_2$-isopropyl ether to give the title compound; mp 172° – 174° C, $[\alpha]_D^{25} = +18.9°$ (c = 1, DMF).

EXAMPLE 8

N$^\epsilon$-t-Butyloxycarbonyl-D-lysyl-D-tryptophyl-D-phenylalanine Methyl Ester Acetate (H—D—Lys—D—Trp—D—Phe—OMe . CH$_3$CO$_2$H)
|
Boc A mixture of

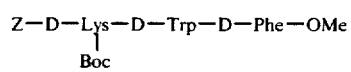

Z—D—Lys—D—Trp—D—Phe—OMe
|
Boc (2.218 g, 3.04 mmoles, described in Example 7) and 5% Pd/C (0.25 g) in acetic acid is rapidly stirred under an atmosphere of hydrogen for 20 hr. The catalyst is removed by filtration and the filtrate evaporated under reduced pressure to give the title compound as an oil: nmr (CDCl$_3$) δ 1.4 (s, 9H), 2.07 (s, 3H), 3.6 (s, 3H).

EXAMPLE 9

Benzyloxycarbonyl-(O-t-butyl)-D-threonyl-N$^\epsilon$-t-butyloxycarbonyl-D-lysyl-D-tryptophyl-D-phenylalanine Methyl Ester (Z—D—Thr—D—Lys—D—Trp—D—Phe—OMe)
|        |
Bu$^t$   Boc A solution of

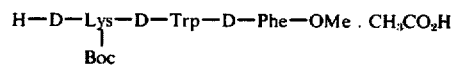

H—D—Lys—D—Trp—D—Phe—OMe . CH$_3$CO$_2$H
|
Boc (3.04 mmoles, described in Example 8),

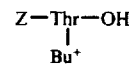

Z—Thr—OH
|
Bu$^t$ (0.940 g, 3.04 mmoles) and 1-hydroxybenzotriazole (0.820 g, 6.08 mmoles) in dry DMF (5 ml), is cooled to 0° C and N-ethylmorpholine (0.39 ml, 3.04 mmoles) is added. A cold (0° C) solution of DCC (0.626 g, 3.04 mmoles) in DMF (4 ml) is added dropwise and the reaction mixture is stirred 1 hr at 0° C and 1 hr at room temperature. After filtration the DMF is removed under reduced pressure. The oily residue obtained after drying is subjected to chromatography on a column of silica gel (270 g) with 2% MeOH in CHCl$_3$ as eluent. The chromatographically pure product is crystallized from MeOH/isopropyl ether to give the title compound; mp 124° – 126° C, $[\alpha]_D^{25} = +3.9°$ (c = 1, DMF).

EXAMPLE 10

Benzyloxycarbonyl-(O-t-butyl)-D-threonyl-N$^\epsilon$-t-butyloxycarbonyl-D-lysyl-D-tryptophyl-D-phenylalanine Hydrazide (II. Z—D—Thr—D—Lys—D—Trp—D—Phe—NHNH$_2$)
|        |
Bu$^t$   Boc A solution of

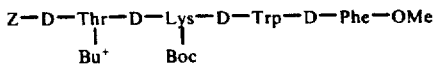

(1.307 g, 1.475 mmoles, described in Example 9) and hydrazine hydrate (2.74 ml) in DMF (8 ml) is stirred at 0° C for 2 hr. Water is added, and the precipitate is collected by filtration and dried (1.267 g) over phosphorus pentoxide. The dried residue is crystallized from MeOH-CH$_2$Cl$_2$-isopropylether to give the title compound; mp 203° – 204° C, $[\alpha]_D^{25} = +11.6°$ (c = 1, DMF).

EXAMPLE 11

Benzyloxycarbonyl-D-asparaginyl-N$^\epsilon$-t-butyloxycarbonyl-D-lysine Methyl Ester (Z—D—Asn—D—Lys—OMe)
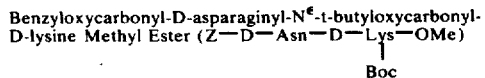

A solution of Z-D-Asn-OTcp (1.48 g, 6.0 mmole) and

H—D—Lys—OMe
|
Boc (2.67 g, 6.0 mmole) in DMF (40 ml) and N-ethylmorpholine (0.5 ml) is stirred at 0° C for 3 hr and at 25° C for 20 hr. The solvent is removed under reduced pressure and the residue triturated with ether. The residue is dried under reduced pressure to give the title compound; mp 147° – 149° C, nmr (MeOH-d$_4$): δ 1.4 (s, 9H), 3.7 (s, 3H), 5.15 (s, 2H), 7.37 (s, 5H).

The mixture is filtered and 1N hydrochloric acid (4.67 ml, 4.67 mmoles) is added to the filtrate. The filtrate is concentrated under reduced pressure, MeOH (50 ml) is added, and the solvent is removed under reduced pressure to give H—D—Asn—D—Lys—OMe . HCl.
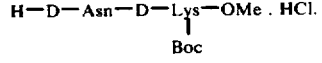

A solution of the above compound (0.88 g, 2.14 mmoles) Z-D-Phe-OTcp (1.023 g, 2.14 mmoles), and N-ethylmorpholine (1 ml) in dry THF (30 ml) is stirred at 0° C for 24 hr. The precipitate is collected by filtration and crystallized from MeOH-isopropyl ether to give the title comound; mp 173° – 175° C, $[\alpha]_D^{25} = +13.4°$ (c = 1, DMF).

EXAMPLE 13

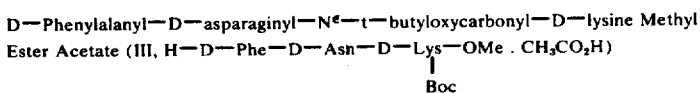

A mixture of

Z—D—Phe—D—Asn—D—Lys—OMe
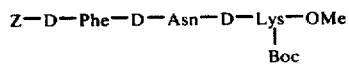

(0.641 g, 0.994 mmole, described in Example 12) and 5% Pd/C (0.065 g) in acetic acid (9 ml) is rapidly stirred under at atmosphere of hydrogen for 20 hr. The mixture is filtered and the filtrate is evaporated under reduced pressure. The residue is dissolved in benzene, and evaporated under reduced pressure (twice) and dried under reduced pressure over KOH pellets to give the title compound as an oil: nmr (CDCl$_3$) δ 1.38 (s, 9H), 2.02 (s, 3H), 3.7 (s, 3H), 7.4 (m, 5H).

EXAMPLE 14

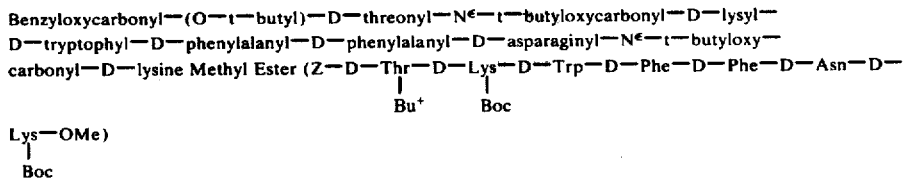

Lys—OMe)
|
Boc

EXAMPLE 12

Benzyloxycarbonyl-D-phenylalanine-D-asparaginyl-N$^\epsilon$-t-butyloxycarbonyl-D-lysine Methyl Ester (Z—D—Phe—D—Asn—D—Lys—OMe)
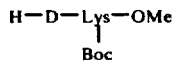

A mixture of

Z—D—Asn—D—Lys—OMe
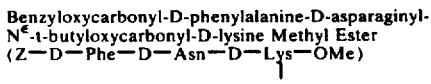

(2.32 g, 4.67 mmoles, described in Example 11) and 5% Pd/C (0.30 g) in acetic acid (30 ml) is rapidly stirred under an atmosphere of hydrogen for 1.5 hours.

Z—D—Thr—D—Lys—D—Trp—D—Phe—NHNH$_2$
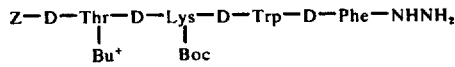

(0.88 g, 0.994 mmole, described in Example 10) is dissolved in dry DMF (20 ml) with slight heating and the clear solution is cooled to −20° C. Hydrochloric acid in EtOAc (2N: 1.25 ml) is added followed by t-butyl nitrite (0.137 ml, 1.2 mmole). The mixture is stirred for 15 min at −15° C. The mixture is stirred for 15 min at −15° C. A solution of

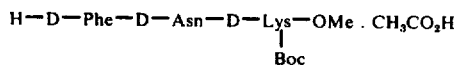

evaporated under reduced pressure (twice) and dried under reduced pressure over KOH pellets to give the title compound as an oil: nmr (CDCl$_3$) δ 0.95 (s, 9H), 1.50 (s, 9H), 2.04 (s, 3H), 3.81 (s, 3H).

EXAMPLE 16

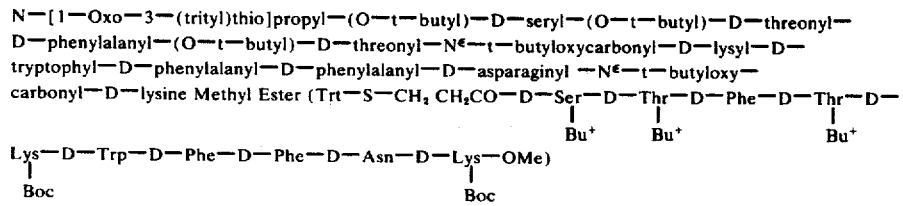

(0.994 mmole, described in Example 13) in DMF (6 ml) containing N-ethyldiisopropylamine (0.60 ml, 3.5 mmoles) is cooled to −15° C and added dropwise to the above mixture. Stirring is continued at −15° C for 1 hr and at room temperature overnight. The reaction mixture is evaporated under reduced pressure at 35° C, the residue triturated with ice cold citric acid (1N), the mixture is filtered and the precipitate is washed with water and dried over phosphorus pentoxide (1.27 g). The solid residue is subjected to chromatography on a column of silica gel (127 g) with 5% MeOH in CHCl$_3$ as eluent. The chromatographically pure product is evaporated under reduced pressure and the residue is crystallized from MeOH-CH$_2$Cl$_2$-isopropyl ether to give the title compound; mp 213°-215° C, [α]$_D^{25}$ = +13.4° (c = 1, DMF).

EXAMPLE 15

(O—t—Butyl)—threonyl —N$^\epsilon$—t—butyloxycarbonyl—D—lysyl—D—tryptophyl—D—phenylalanyl—D—phenylalanyl—D—asparaginyl—N$^\epsilon$—t—butyloxycarbonyl—D—lysine Methyl Ester Acetate (IV, H—D—Thr—D—Lys—D—Trp—D—Phe—D—Phe—D—Asn—D—Lys—OMe . CH$_3$CO$_2$H)
|     Bu$^+$   Boc                                              Boc A mixture of

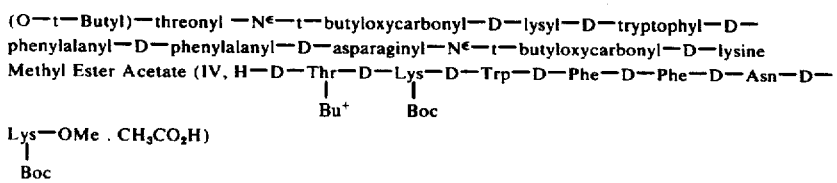

(0.71 g, 0.515 mmole, described in Example 14) and 5% Pd/C (0.065 g) in acetic acid is rapidly stirred under an atmosphere of hydrogen for 20 hr. The mixture is filtered and the filtrate evaporated under reduced pressure. The residue is dissolved in benzene, The tripeptide hydrazide (V)

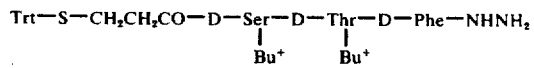

(0.418 g, 0.515 mmole, described in Example 5) is dissolved in dry DMF (6 ml) and cooled to −20° C. Hydrogen chloride in EtOAc (2N, 0.645 ml) is added followed by t-butyl nitrite (0.0706 ml, 0.619 mmole). The mixture is stirred for 15 min at −15° C. A solution of

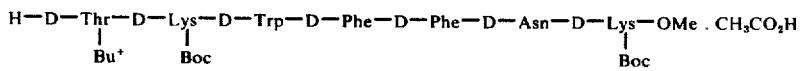

(0.515 mmole, described in Example 15) in DMF (10 ml) containing N-ethyldiisopropylamine (0.310 ml, 1.8 mmole) is cooled to −15° C and added dropwise to the above mixture. Stirring is continued at −15° C for 1 hr and at room temperature overnight. The reaction mixture is evaporated under reduced pressure at 35° C, the residue is triturated with ice cold citric acid (1N), filtered, washed with water and dried over phosphorus pentoxide. The solid residue is subjected to chromatography on a column of silica gel (100 g) with 5% MeOH in CHCl$_3$ as eluent. The chromatographically pure product is crystallized from MeOH/CH$_2$Cl$_2$/isopropyl ether to give the title compound mp 205° − 207° C [α]$_D^{25}$ = +4.3° (c = 1, DMF).

EXAMPLE 17

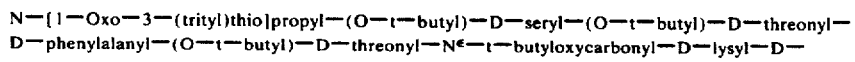

-continued

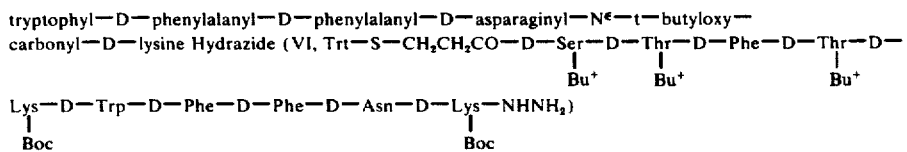

A solution of

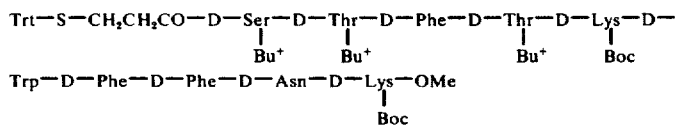

(0.504 g, 0.249 mmole, described in Example 16) in DMF (6 ml) and hydrazine hydrate (0.464 ml) is stirred at 0° C for 30 min and at room temperature for 23 hr. The product is precipitated by addition of cold water and filtered. The precipitate is washed several times with water and dried under reduced pressure over phosphorus pentoxide to give the title compound: amino acid analysis: Lys, 1.91, Thr, 1.62, Ser, 0.76, Asp, 1.00, Phe, 2.90.

EXAMPLE 18

N,S—Ditrityl—D—cysteinylglycine—ethylamide (Trt—D—Cys—Gly—NHE$^+$)
<br>|<br>Trt

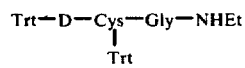

(1.03 g, 1.52 mmoles, described in Example 18) in acetic acid (8 ml) and water (1.9 ml) is stirred at 45° C for 15 min. Water (8 ml) is added and the precipiate is removed by filtration. Hydrochloric acid (1N, 1.5 ml) is added to the filtrate and the solution lyophilized. The dry product is washed with ether to give the title compound; nmr (DMSO-$d_6$) δ 1.02 (t J=7 Hz, 3H), 3.20 (m, 2H), 7.40 (s, 15H).

EXAMPLE 20

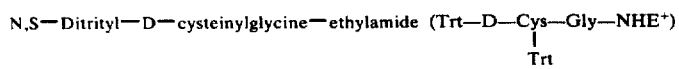

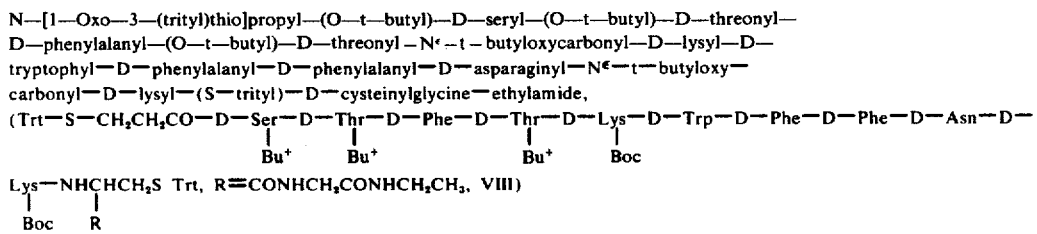

A solution of

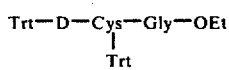

(10 g, prepared as described by G. Amiard, Bull. Soc. Chim. (Fr.), 1956, 698 for the L-isomer of cysteine) and ethylamine (15 ml) is allowed to stand at 5° C for 24 hr. The solution is evaporated under reduced pressure and the residue is subjected to chromatography on a column of silica gel (200 g) using 15% to 30% EtOAc in benzene as eluent. The eluants are evaporated under reduced pressure to give the title compound; nmr (CDCl$_3$) δ 0.9 (t, J = 7 Hz, 3H), 7.35 (m, 30H).

EXAMPLE 19

S—Trityl—D—cysteinylglycine—ethylamide hydrochloride
(HNHCHCH$_2$S Trt, R=CONHCH$_2$CONHCH$_2$CH$_3$,VIIb)
<br>|<br>R A solution of

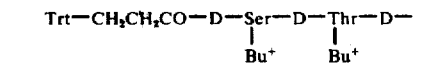

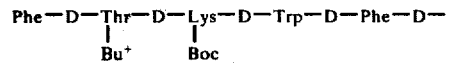

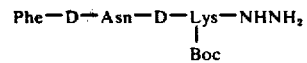

(0.467 g, 0.231 mmole, described in Example 17) is dissolved in a mixture of dry distilled DMF (8 ml) and DMSO (2 ml) and cooled to −20° C. Hydrogen chloride in EtOAc (1.4 N; 0.412 ml, 0.577 mmole) is added followed by t-butyl nitrite (0.0313 ml, 0.276 mmole). The mixture is stirred for 15 min at −15° C. A solution of

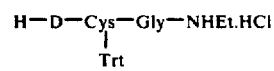

(0.112 g, 0.231 mmole, described in Example 19) in DMF (2.5 ml) containing N-ethyldiisopropylamine (0.138 ml), 0.807 mmole) is cooled to −15° C and added dropwise to the above reaction mixture. Stirring is continued at −15° C for 1 hr and at room temperature overnight. The reaction mixture is evaporated under reduced pressure, the residue is triturated with ice cold citric acid (1N), filtered and washed with water. The solid residue is washed 3 times with MeOH and dried under reduced pressure to give the title compound; amino acid analysis: ratio Asp/Gly = 1.08:1.

EXAMPLE 21

Cyclic Disulfide of N—(1—oxo—3—thio)propyl—(O—t—butyl)—D—seryl—(O—t—butyl)—D—threonyl—D—phenylalanyl—(O—t—butyl)—D—threonyl—N$^\epsilon$—t—butyloxycarbonyl—D—lysyl—D—tryptophyl—D—phenylalanyl—D—phenylalanyl—D—asparaginyl—N$^\epsilon$—t—butyloxycarbonyl—D—lysyl—D—cysteinylglycine—ethylamide (S—CH$_2$CH$_2$CO—D—Ser—D—Thr—D—

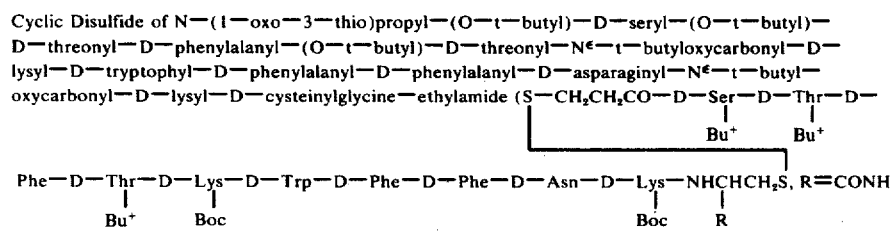

Phe—D—Thr—D—Lys—D—Trp—D—Phe—D—Phe—D—Asn—D—Lys—NHCHCH$_2$S, R=CONHCH$_2$CONHCHCH$_3$, IX)
     |          |                                         |    R
Bu$^+$  Boc                                         Boc

A solution of

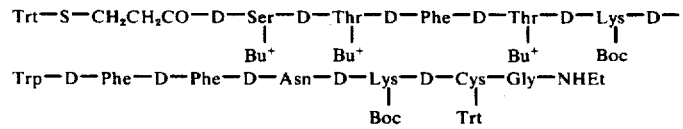

(0.32 g, 0.132 mmole, described in Example 20) in acetic acid is slowly added to a stirred solution of iodine (0.336 g, 1.32 mmole) in MeOH (66 ml) at room temperature. After completion of addition the solution is stirred at room temperature for 1 hr. The solution is cooled to 0° C and a solution of sodium thiosulfate in water (1N) is slowly added to destroy the excess of iodine until a colorless solution is obtained. The solvent is evaporated under reduced pressure almost to dryness; the residue is dissolved in MeOH and added to ice cold water. The precipitate is collected by filtration, washed with water and dried under reduced pressure over phosphorus pentoxide to give the title compound; amino acid analysis: Lys, 1.92; Ser, 0.75; Asp, 1.05; Gly, 1.00; Thr, 1.78; Phe, 3.02; Cysteic acid, 0.93.

EXAMPLE 22

A solution of the cyclic disulfide of

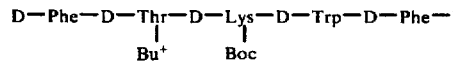

(0.250 g, 0.132 mmole, described in Example 21) is vigorously stirred at 0° C under an atmosphere of nitrogen for 10 min in conc. hydrochloric acid (11 ml). Acetic acid (150 ml) is added and the solution is lyophilized. The residue is taken in water, filtered and again lyophilized. The residue (0.20 g) is dissolved in 0.01 M ammonium acetate (10 ml), the solution obtained is applied to a column (2.1 × 30 cm) of carboxymethyl cellulose (Whatman CM-23) and eluted first with 0.01M ammonium acetate (200 ml), to remove the impurities. The pure compound is eluted with 0.05 M and 0.06 M ammonium acetate and lyophilized to give the title compound as a white solid in the form of its acetic acid addition salt; $\nu_{max}^{MeOH}$ 289 (6310), 283 nm ($\epsilon$ 6310). Repeated lyophilization of the latter product from water gives the title compound as the free base; amino acid analysis: Lys, 1.88; Asp, 1.00; Thr, 1.89; Ser, 0.92; Gly, 0.71; Cys, 0.43; Phe, 2.93. Lyophilization of the latter product from 1N hydrochloric acid gives the title compound in the form of its hydrochloric acid addition salt; amino acid analysis: Lys, 1.92; Asp, 1.00; Thr, 1.90; Ser, 0.90; Gly, 0.78; Cys, 0.52; Phe, 2.90.

EXAMPLE 23

N—(1—Oxo—3—thio)propyl—D—seryl—D—threonyl—D—phenylalanyl—D—threonyl—D—lysyl—D—tryptophyl—D—phenylalanyl—D—phenylalanyl—D—asparaginyl—D—lysyl—D—Cyclic Disulfide of N—(1—oxo—3—thio)propyl—D—seryl—D—threonyl—D—phenyl—alanyl—D—threonyl—D—lysyl—D—tryptophyl—D—phenylalanyl—D—phenylalanyl—D—asparaginyl—D—lysyl—D—cysteinylglycine—ethylamide

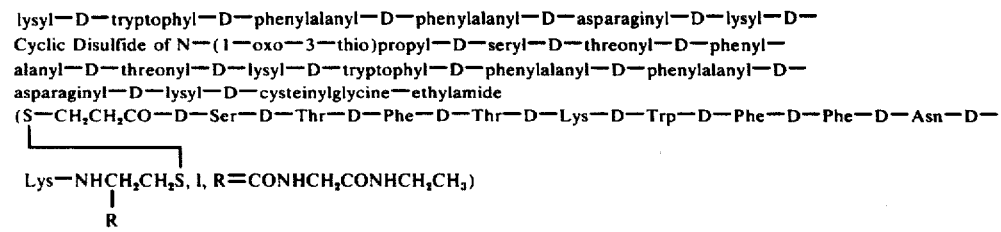

Lys—NHCH$_2$CH$_2$S, I, R=CONHCH$_2$CONHCH$_2$CH$_3$)
      |
      R

-continued cysteinylglycine—ethylamide (H—S—CH₂CH₂CO—D—Ser—D—Thr—D—Phe—D—Thr—D—Lys—D—Trp—D—Phe—D—Phe—D—Asn—D—Lys—NHCH₂CH₂SH, 1a, R=CONHCH₂CONHCH₂CH₃)
|
R By following the procedure of Example 22 but replacing the title cyclic disulfide of Example 21 with an equivalent amount of the title compound of Example 20

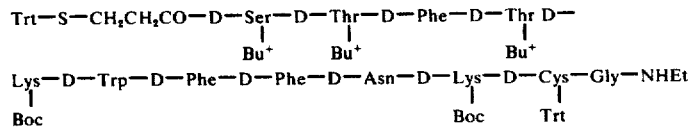

the title compound of this example is obtained; amino acid analysis: Lys, 2.02; Asp, 1.00; Thr, 1.95; Ser, 0.88; Gly, 0.82; Cys, 0.49; Phe, 2.97.

In the same manner, by replacing the title compound of Example 20 with the corresponding disulfhydryl derivative of formula X in which R is

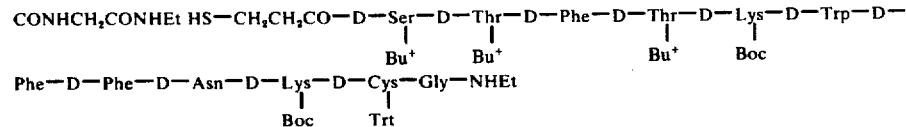

and proceding as above the title compound is also obtained.

EXAMPLE 24

N—[1—Oxo—3—(trityl)thio]propyl—(O—t—butyl)—D—seryl—(O—t—butyl)—D—threonyl—D—phenylalanyl—(O—t—butyl)—D—threonyl—Nε—t—butyloxycarbonyl—D—lysyl—D—tryptophyl—D—phenylalanyl—D—phenylalanyl—D—asparaginyl—Nε—t—butyloxycarbonyl—D—lysine 2—(tritylthio)ethylamide (Trt—S—CH₂CH₂CO—D—Ser—D—Thr—D—Phe—D—Thr—D—Lys—D—Trp—D—Phe—D—Phe—D—Asn—D—Lys—NHCH₂CH₂S Trt, VIII, R = H)

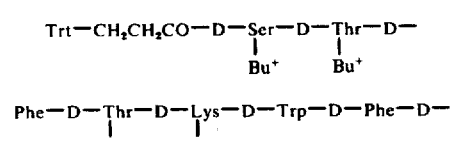

(0.458 g, 0.227 mmole, described in Example 17) is dissolved in a mixture of dry distilled DMF (8 ml) and DMSO (2 ml) and cooled to −20° C. Hydrogen chloride in EtOAc (2.0 N; 0.286 ml, 0.567 mmole) is added followed by t-butyl nitrite (0.0314 ml, 0.276 mmole). The mixture is stirred for 15 min at −15° C. A solution of 2-tritylthioethylamine [0.080 g, 0.250 mmole, prepared as described by F. I. Carroll et al., J. Org. Chem., 30, 36 (1965)] in DMF (3 ml) containing N-ethyldiisopropylamine (0.055 ml, 0.348 mmole) is cooled to 15° C and added dropwise to the above reaction mixture. Stirring is continued at −15° C for 1 hr and at room temperature for 3 days. The reaction mixture is evaporated under reduced pressure, the residue is triturated with ice cold citric acid (1N) and filtered. The precipitate is washed with water, dried and crystallized from chloroform-methanol to give the title compound, mp 234° – 237° C. anal: calcd for C₁₃₀H₁₆₅N₁₅O₁₉S₂: C, 67.71; H, 7.21; N, 9.11. Found: C, 67.64; H, 7.28; N, 9.24.

EXAMPLE 25

Cyclic Disulfide of N—(1—Oxo—3—thio)propyl—(O—t—butyl)—D—seryl—(O—t—butyl)—D—threonyl—D—phenylalanyl—(O—t—butyl)—D—threonyl—Nε—t—butyloxycarbonyl—D—lysyl—D—tryptophyl—D—phenylalanyl—D—phenylalanyl—D—asparaginyl—Nε—t—butyloxycarbonyl—D—lysine 2—thioethylamide

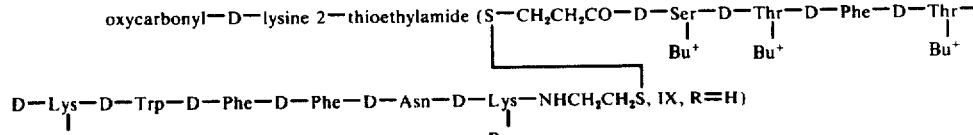

A solution of

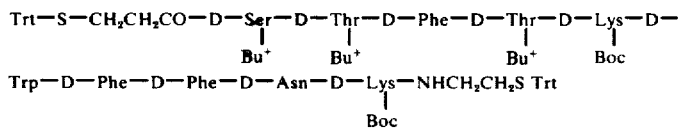

(0.220 g, 0.096 mmole, described in Example 24) in acetic acid (40 ml) is slowly added to a stirred solution of iodine (0.956 mmole) in acetic acid (50 ml) at room temperature. After completion of addition, the solution is stirred at room temperature for 1 hr. The solution is cooled to 0° C and a solution of sodium thiosulfate in water (1N) is slowly added to destroy the excess of iodine until a colorless solution is obtained. The solvent is evaporated under reduced pressure almost to dryness and the residue is triturated with water. The precipitate is collected by filtration and dried under reduced pressure over phosphorus pentoxide to give the title compound; amino acid analysis: Lys, 1.89; Ser, 0.71; Asp, 1.06; Thr, 1.75; Phe 3.12.

column of a chemically modified crosslinked dextran ("Sephadex G-25 M", 3 × 50 cm, equilibrated in the lower phase of n-butanol-acetic acid-water (4:1:5) and then equilibrated in the upper phase) using the upper phase to desorb the cyclic peptide. The fractions containing the pure cyclic peptide are combined and lyophilized to give the title compound in the form of its acetic acid addition salt; $\lambda_{max}^{MeOH}$ 290 ($\epsilon$ 5,415), 282 ($\epsilon$ 6,000) and 274 nm ($\epsilon$ 5,660). Repeated lyophilization of the latter compound from water gives the title compound in the form of its free base; amino acid analysis: Lys, 2.10; Asp, 0.93; Thr, 1.83; Ser, 0.93; Phe, 3.00.

EXAMPLE 27

N—(1—Oxo—3—thio)propyl—D—seryl—D—threonyl—D—phenylalanyl—D—threonyl—D—lysl—D—tryptophyl—D—phenylalanyl—D—phenylalanyl—D—asparaginyl—D—lysine 2—thioethylamide (H—S—CH₂CH₂CO—D—Ser—D—Thr—D—Phe—D—Thr—D—Lys—D—Trp—D—Phe—D—Phe—D—Asn—D—Lys—NHCH₂CH₂SH, Ia, R = H)

EXAMPLE 26

Cyclic Disulfide of N—(1—Oxo—3—thio)propyl—D—seryl—D—threonyl—D—phenyl—alanyl—D—threonyl—D—lysyl—D—tryptophyl—D—phenylalanyl—D—phenylalanyl—D—asparaginyl—D—lysine 2—thioethylamide

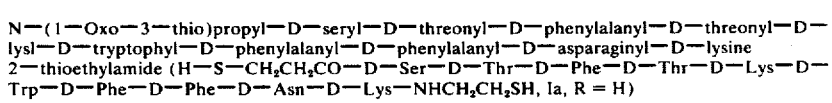

A solution of the cyclic disulfide of

By following the procedure of Example 26 but replacing the title cyclic disulfide of Example 25 with an equivalent amount of the title compound of Example

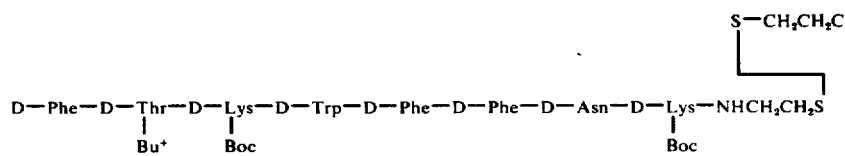

(0.096 mmole, described in Example 25) is vigorously stirred at 0° C under an atmosphere of nitrogen for 10 min in conc. hydrochloric acid (10 ml). Acetic acid (100 ml) is added and the solution is lyophilized. The residue is taken up in 5% acetic acid in water and again lyophilized. The residue is dissolved in the upper phase of n-butanol-acetic acid-water (4:1:5) and filtered. The filtrate is subjected to partition chromatography on a

24

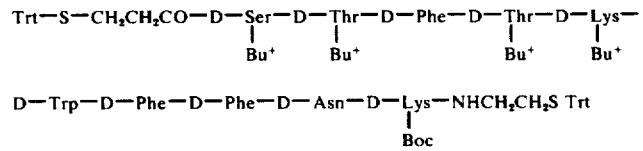

the title compound of this example is obtained; amino acid analysis: Lys, 1.95; Asp, 1.13; Thr, 1.91; Ser, 0186; Phe, 3.00.

In the same manner, but replacing the title compound of Example 24 with the corresponding disulfhydryl derivative of formula X in which R is hydrogen

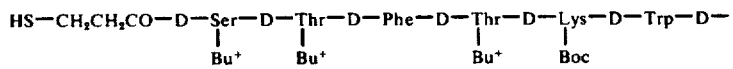

-continued

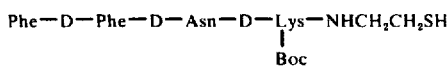
Boc and proceeding as above the title compound is also obtained.

We claim:

1. A process for preparing a peptide of formula I

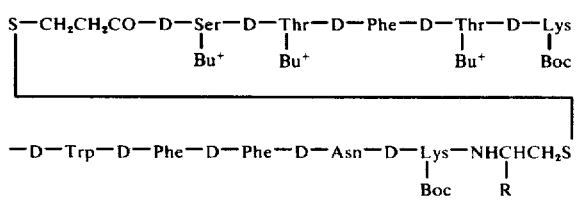

in which R is hydrogen or CONHCH$_2$CONHCH$_2$CH$_3$ which comprises: reacting a decapeptide of formula VI

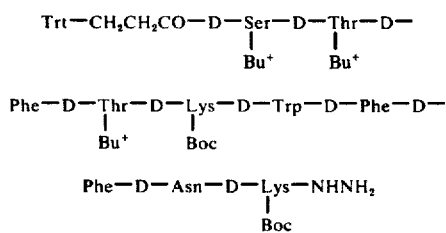

with a reagent that furnishes nitrous acid in situ in the presence of a strong acid to convert said decapeptide to the corresponding azide and reacting said azide with a compound of formula VII,

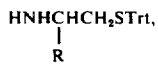

in which R is as defined herein to obtain the corresponding linear protected peptide of formula VIII

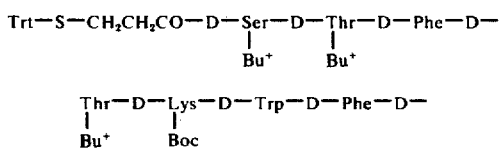

in which R is as defined herein followed by oxidizing said linear protected peptide with iodine or thiocyanogen to obtain the corresponding cyclic disulfide derivative of formula IX

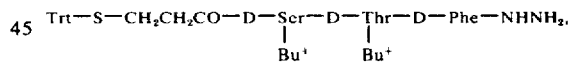

in which R is as defined herein and subsequently treating said cyclic derivative in the presence of a concentrated organic acid or an aqueous solution of a mineral acid under moderately acidic conditions appropriate to remove the Bu$^+$ or Boc protecting groups to obtain the corresponding peptide of formula I; or followed by subjecting said linear peptide to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative of formula X by treatment with hydrogen sulfide, oxidizing said last-named derivative by treatment with oxygen, 1,2-diiodoethane, sodium, or potassium ferricyanide or iodine to obtain the corresponding cyclic disulfide and treating said cyclic disulfide in the presence of a concentrated organic acid or an aqueous solution of a mineral acid under moderately acidic conditions appropriate to remove the Bu$^+$ or Boc protecting groups to obtain the desired peptide of formula 1.

2. A process as claimed in claim 1 in which the decapeptide of formula VI is prepared by reacting a tripeptide of formula V,

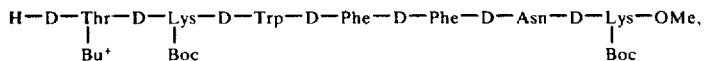

with a reagent that furnishes nitrous acid in situ in the presence of a strong acid to convert said tripeptide to the corresponding azide and reacting said azide with a heptapeptide of formula IV, H—D—Thr—D—Lys—D—Trp—D—Phe—D—Phe—D—Asn—D—Lys—OMe,
     |          |                                          |
     Bu$^+$     Boc                                        Boc to obtain the decapeptide of formula

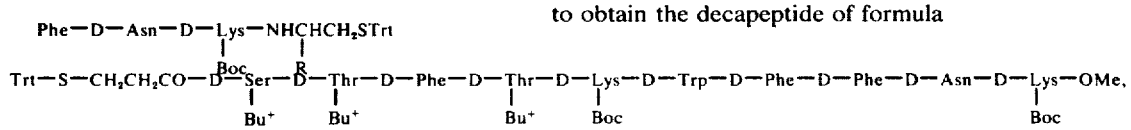

followed by reacting said last-named compound with hydrazine hydrate and isolating said decapeptide of formula VI.

3. A process as claimed in claim 1 in which the compound of formula VII,

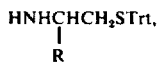

in which R is CONHCH$_2$CONHCH$_2$CH$_3$ (VIIb) is prepared by reacting the dipeptide of formula

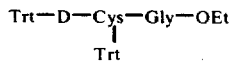

with ethylamine to obtain the corresponding dipeptide of formula

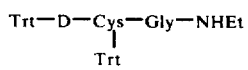

and removing the terminal amino protecting group (Trt) of said last-named compound under mildly acidic conditions in the presence of a dilute aqueous solution of an organic acid to obtain said compound of formula

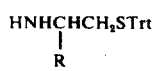

in which R is CONHCH$_2$CONHCH$_2$CH$_3$.

4. A process as claimed in claim 2 in which the tripeptide of formula V,

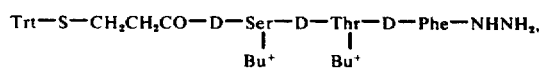

is prepared by reacting a tripeptide of formula

H—D—Ser—D—Thr—D—Phe—OMe
    |         |
    Bu$^+$    Bu$^+$ with an activated ester of

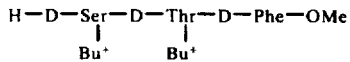

followed by reacting the last-named compound with hydrazine hydrate and isolating said tripeptide of formula V.

5. A process as claimed in claim 4 in which the tripeptide of formula

H—D—Ser—D—Thr—D—Phe—OMe
    |         |
    Bu$^+$    Bu$^+$ is prepared by reacting a dipeptide of formula H—D—Thr—D—Phe—OMe
         |
         Bu$^+$ with an activated ester of

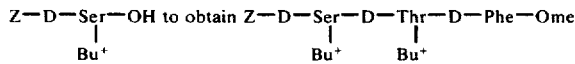

and removing the terminal amino protecting group (Z) of said last-named compound by hydrogenation in the presence of a noble metal catalyst to obtain said tripeptide.

6. A process as claimed in claim 5 in which the dipeptide of formula

H—D—Thr—D—Phe—OMe
         |
         Bu$^+$ is prepared by reacting H-D-Phe-OMe with an activated ester of

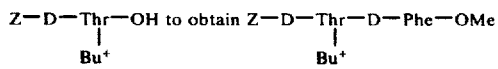

and removing the terminal amino protecting group (Z) of said last-named compound by hydrogenation in the presence of a noble metal catalyst to obtain said dipeptide.

7. A process as claimed in claim 2 in which the heptapeptide of formula IV,

H—D—Thr—D—Lys—D—Trp—D—Phe—D—Phe—D—Asn—D—Lys—Ome,
    |         |                              |
    Bu$^+$    Boc                            Boc is prepared by reacting the tetrapeptide of formula II, Z—D—Thr—D—Lys—D—Trp—D—Phe—NHNH$_2$,
    |         |
    Bu$^+$    Boc with a reagent that furnishes nitrous acid in situ in the presence of a strong acid to convert said tetrapeptide to the corresponding azide and reacting said azide with a tripeptide of formula III, H—D—Phe—D—Asn—D—Lys—Ome,
                    |
                    Boc to obtain a heptapeptide of formula Z—D—Thr—D—Lys—D—Trp—D—Phe—D—Phe—D—Asn—D—Lys—Ome
     |        |                                              |
     Bu⁺     Boc                                            Boc and removing the terminal amino protecting group (Z) of said last-named compound by hydrogenation in the presence of a noble metal catalyst and isolating said heptapeptide.

8. A process as claimed in claim 7 in which the tetrapeptide of formula II,

Z—D—Thr—D—Lys—D—Trp—D—Phe—NHNH₂,
     |        |
     Bu⁺     Boc is prepared by reacting a tripeptide of formula H—D—Lys—D—Trp—D—Phe—OMe
      |
      Boc with an activated ester of Z—D—Thr—OH
     |
     Bu⁺ to obtain a tetrapeptide of formula

Z—D—Thr—D—Lys—D—Trp—D—Phe—OMe,
     |        |
     Bu⁺     Boc followed by reacting said last-named compound with hydrazine hydrate and isolating said tetrapeptide.

9. A process as claimed in claim 8 in which the tripeptide of formula

H—D—Lys—D—Trp—D—Phe—OMe,
      |
      Boc is prepared by reacting a dipeptide of formula H-D-Trp-D-Phe-OMe with an activated ester of Z—D—Lys—OH
      |
      Boc to obtain a tripeptide of formula Z—D—Lys—D—Trp—D—Phe—Ome
      |
      Boc and removing the terminal protecting group (Z) of said last-named compound by hydrogenation in the presence of a noble metal catalyst to obtain said tripeptide.

10. A process as claimed in claim 9 in which the dipeptide of formula H-D-Trp-D-Phe-OMe is prepared by reacting H-D-Phe-OMe with an activated ester of Z-D-Trp-OH to obtain a dipeptide of formula Z-D-Trp-D-Phe-OMe and removing the terminal amino protecting group (Z) of said last-named compound by hydrogenation in the presence of a noble metal catalyst to obtain said dipeptide.

11. A process as claimed in claim 7 in which the tripeptide of formula III.

H—D—Phe—D—Asn—D—Lys—OMe ,
                         |
                         Boc is prepared by reacting a dipeptide of formula H—D—Asn—D—Lys—OMe
                |
                Boc with an activated ester of Z-D-Phe-Oh to obtain a tripeptide of formula Z—D—Phe—D—Asn—D—Lys—OMe
                         |
                         Boc and removing the terminal amino protecting group (Z) of said last-named compound by hydrogenation in the presence of a noble metal catalyst to obtain said tripeptide.

12. A process as claimed in claim 11 in which the dipeptide of formula

H—D—Asn—D—Lys—OMe
                |
                Boc is prepared by reacting

H—D—Lys—OMe
      |
      Boc with an activated ester of Z-D-Asn-OH to obtain a dipeptide of formula Z—D—Asn—D—Lys—OMe
                |
                Boc and removing the terminal amino protecting group (Z) of said last-named compound by hydrogenation in the presence of a noble metal catalyst to obtain said dipeptide.

13. A process as claimed in claim 1 in which the linear protected peptide of formula VIII as defined therein is subjected, in the presence of a concentrated organic acid or an aqueous solution of a mineral acid, to moderately acidic conditions appropriate to remove the Trt, Bu⁺ or Boc protecting groups to obtain the corresponding compound of formula Ia

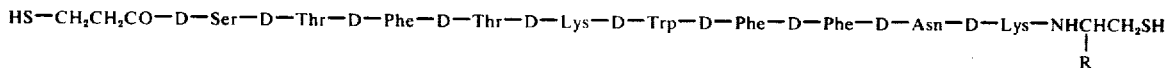

in which R is as defined therein.

14. A process as claimed in claim 1 in which the corresponding disulfhydryl derivative as defined therein is subjected, in the presence of a concentrated organic acid or an aqueous solution of a mineral acid, to moderately acidic conditions appropriate to remove the Bu⁺ or Boc protecting groups to obtain the corresponding compound of formula Ia HS-CH₂CH₂CO-D-Ser-D-Thr-D-Phe-D-Thr-D-Lys-D- Trp-D-Phe-D-Phe-D-Asn-D-Lys-NHCHCH₂SH in which R is as defined therein.

18. The compound of claim 17 in which R is hydrogen.

19. The compound of claim 17 in which R is CONHCH₂CONHCH₂CH₃.

20. A compound of the formula Ia

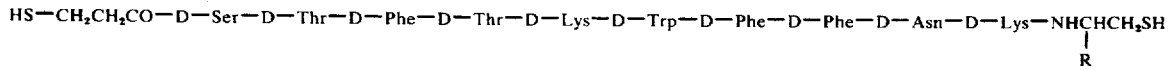

in which R is hydrogen or CONHCH₂CONHCH₂CH₃.

21. The compound of claim 20 in which R is hydrogen.

22. The compound of claim 20 in which R is CONHCH₂CONHCH₂CH₃.

23. A compound of the formula IX

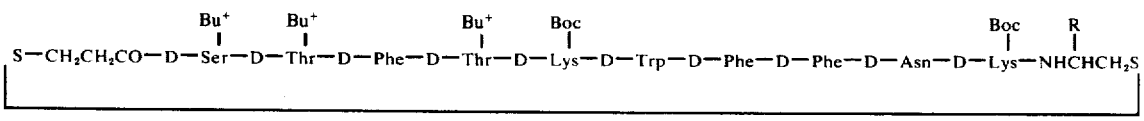

15. The process as claimed in claim 1 wherein said linear protected peptide of formula VIII is subjected to treatment with iodine in the presence of a lower alkanol or acetic acid to obtain the corresponding cyclic disulfide derivative of formula IX.

16. The process as claimed in claim 1 wherein said in which R is hydrogen or CONHCH₂CONHCH₂CH₃.

24. The compound of claim 23 in which R is hydrogen.

25. The compound of claim 23 in which R is CONHCH₂CONHCH₂CH₃.

26. A compound of the formula VIII,

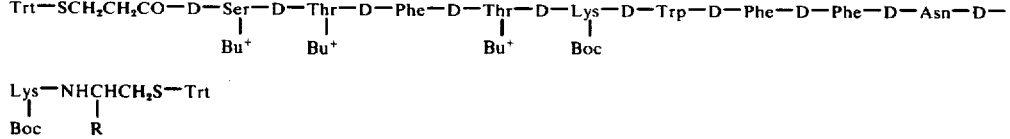

linear protected peptide of formula VIII is subjected to treatment with iodine at from about 0° to 30° C for about 30 to 180 minutes in a lower alkanol or acetic acid to obtain the corresponding cyclic disulfide derivative of formula IX.

17. A compound of the formula I in which R is hydrogen or CONHCH₂CONHCH₂CH₃.

27. The compound of claim 26 in which R is hydrogen.

28. The compound of claim 26 in which R is CONHCH₂CONHCH₂CH₃.

29. A compound of the formula VI

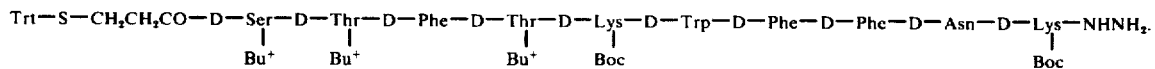

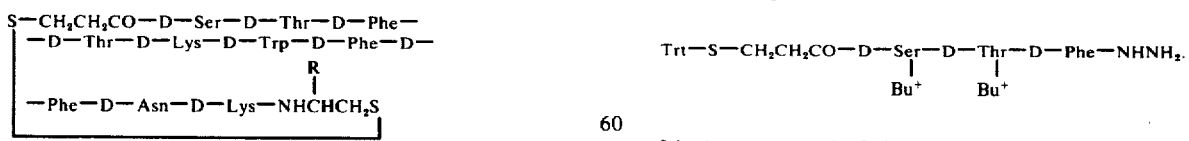

30. A compound of the formula V

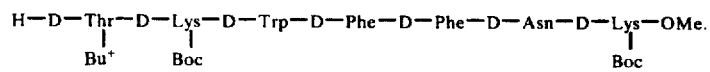

31. A compound of the formula IV

H—D—Thr—D—Lys—D—Trp—D—Phe—D—Phe—D—Asn—D—Lys—OMe.
　　　|　　　　|　　　　　　　　　　　　　　　　　　　　　|
　　　Bu⁺　　Boc　　　　　　　　　　　　　　　　　　　　Boc in which R is hydrogen or CONHCH₂CONHCH₂CH₃.

32. A compound of the formula II

Z—D—Thr—D—Lys—D—Trp—D—Phe—NHNH$_2$.
    |          |
   Bu$^t$     Boc

33. A compound of the formula III

H—D—Phe—D—Asn—D—Lys—OMe.
                    |
                   Boc

34. A compound of the formula VIIb

H—D—Cys—Gly—NHEt.
      |
     Trt

35. A compound of the formula

Trt—S—CH$_2$CH$_2$CO—D—Ser—D—Thr—D—Phe—OMe.
                      |        |
                     Bu$^t$   Bu$^t$

36. A compound of the formula

H—D—Ser—D—Thr—D—Phe—OMe.
     |        |
    Bu$^t$   Bu$^t$

37. A compound of the formula

H—D—Thr—D—Phe—OMe.
     |
    Bu$^t$

38. A compound of the formula

Z—D—Thr—D—Lys—D—Trp—D—Phe—OMe.
    |         |
   Bu$^t$    Boc

39. A compound of the formula

H—D—Thr—D—Lys—D—Trp—D—Phe—OMe.
    |         |
   Bu$^t$    Boc

40. A compound of the formula

H—D—Lys—D—Trp—D—Phe—OMe.
     |
    Boc

41. A compound of the formula H-D-Trp-D-Phe-OMe.

42. A compound of the formula

H—D—Asn—D—Lys—OMe.
              |
             Boc

43. A pharmaceutically acceptable acid addition salt of the compound of formula I as claimed in claim 17.

44. The acid addition salt of claim 43 in which the acid is acetic acid.

45. The acid addition salt of claim 43 in which the acid is hydrochloric acid.

46. A pharmaceutically acceptable acid addition salt of the compound of formula Ia as claimed in claim 20.

47. The acid addition salt of claim 46 in which the acid is acetic acid.

48. The acid addition salt of claim 46 in which the acid is hydrochloric acid.

49. A pharmaceutical composition which comprises a compound of the formula I as claimed in claim 17 and a pharmacologically acceptable carrier therefor.

50. A pharmaceutical composition which comprises a compound of the formula Ia as claimed in claim 20 and a pharmaceutically acceptable carrier therefor.

51. A method of treating diabetes which comprises administering a therapeutically effective amount of a compound of formula I as claimed in claim 17 together with a pharmaceutically acceptable carrier therefor.

52. A method of treating diabetes which comprises administering a therapeutically effective amount of a compound of formula IA as claimed in claim 20 together with a pharmaceutically acceptable carrier therefor.

* * * * *